US008895088B2

(12) United States Patent
Matsunaga et al.

(10) Patent No.: US 8,895,088 B2
(45) Date of Patent: Nov. 25, 2014

(54) METHOD FOR IMPROVEMENT OF FOODS UTILIZING β-AMYLASE

(75) Inventors: Akiko Matsunaga, Kakamigahara (JP); Masamichi Okada, Kakamigahara (JP); Shotaro Yamaguchi, Kakamigahara (JP)

(73) Assignee: Amano Enzyme Inc., Nagoya-Shi, Aichi (JP)

( * ) Notice: Subject to any disclaimer, the term of this patent is extended or adjusted under 35 U.S.C. 154(b) by 0 days.

(21) Appl. No.: 13/383,661

(22) PCT Filed: Dec. 22, 2009

(86) PCT No.: PCT/JP2009/007083
§ 371 (c)(1), (2), (4) Date: Jan. 12, 2012

(87) PCT Pub. No.: WO2011/007404
PCT Pub. Date: Jan. 20, 2011

(65) Prior Publication Data
US 2012/0121760 A1 May 17, 2012

(30) Foreign Application Priority Data

Jul. 17, 2009 (JP) .................................. 2009-168550

(51) Int. Cl.
| | | |
|---|---|---|
| *A21D 8/04* | (2006.01) | |
| *C12N 9/26* | (2006.01) | |
| *A21D 13/00* | (2006.01) | |
| *A23L 1/10* | (2006.01) | |
| *A23L 1/105* | (2006.01) | |
| *C12N 9/28* | (2006.01) | |
| *A23G 3/48* | (2006.01) | |

(52) U.S. Cl.
CPC .................. *A21D 8/042* (2013.01); *A23L 1/105* (2013.01); *C12Y 302/01002* (2013.01); *C12N 9/2411* (2013.01); *C12N 9/2425* (2013.01); *C12N 9/2417* (2013.01); *A23G 3/48* (2013.01)
USPC ............... 426/28; 426/617; 426/531; 426/64; 426/63; 426/61

(58) Field of Classification Search
CPC ........... C12N 9/26; A21D 8/04; A21D 13/00; A23L 1/10
USPC .......................... 426/28, 617, 531, 64, 63, 61
See application file for complete search history.

(56) References Cited

FOREIGN PATENT DOCUMENTS

| CN | 101153276 A | | 4/2008 | |
|---|---|---|---|---|
| DK | WO9104669 | * | 4/1991 | ............... A21D 8/04 |
| JP | 60-002185 A | | 1/1985 | |
| JP | 62-079745 A | | 4/1987 | |
| JP | 03-292846 A | | 12/1991 | |
| JP | H06292505 A | | 10/1994 | |
| JP | 08-089158 A | | 4/1996 | |
| WO | WO-2009/136471 A1 | | 11/2009 | |

OTHER PUBLICATIONS

"Kogyo—yo toushitu," Handbook of Industrial Carbohydrate Enzymes, Kodansha Scientific Ltd., 1999, pp. 24-27.
H. Outtrup et al., "Properties and Application of a Thermostable Maltogenic Amylase Produced by a Strain of *Bacillus* Modified by Recombinant-DNA Techniques," Starch, vol. 36, No. 12, pp. 405-411, 1984.
A. Matsunaga et al, Annual Meeting of Japan Society for Bioscience, Biotechnology, and Agrochemistry 2009, p. 111 (2P0890B).
J.-S. Lee et al., "Cloning, expression, and carbon catabolite repression of the bamM gene encoding β—amylase of *Bacillus megaterium* DSM319," Appl Microbiol Biotechnol vol. 56, No. 1-2, 2001, pp. 205-211.
International Search Report dated Mar. 9, 2010, issued for PCT/JP2009/007083.
International Biodeterioration & Biodegradation, 2008 (online), vol. 63, p. 106-111.

* cited by examiner

*Primary Examiner* — Hamid R Badr
(74) *Attorney, Agent, or Firm* — Edwards Wildman Palmer LLP; James E. Armstrong, IV; Gabriel J. McCool

(57) ABSTRACT

A novel β-amylase having excellent practical applicability is found, and an object is to provide a practical use of the β-amylase. Provided is a method for improving a food, wherein a β-amylase obtained from *Bacillus flexus* is acted on a food containing a polysaccharide or an oligosaccharide having an α-1,4 bond of glucose as the main chain.

8 Claims, 9 Drawing Sheets

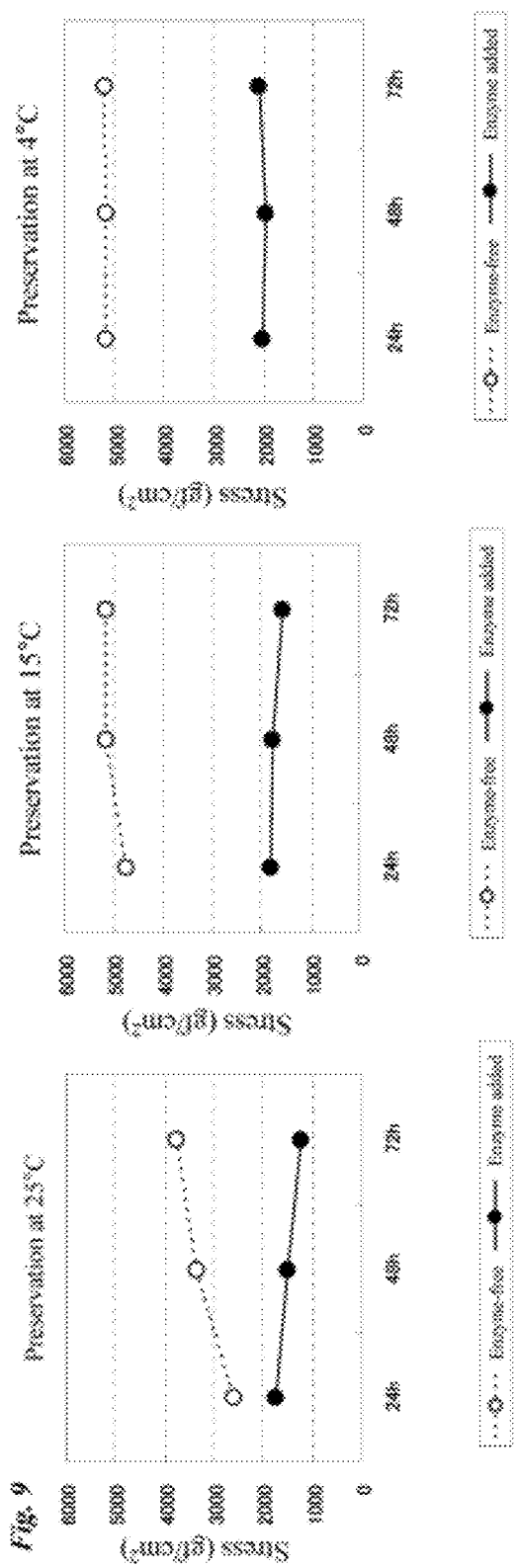

SEQUENCE LISTING

```
<160> NUMBER OF SEQ ID NOS: 9

<210> SEQ ID NO 1
<211> LENGTH: 10
<212> TYPE: PRT
<213> ORGANISM: Bacillus flexus

<400> SEQUENCE: 1

Ala Val Asn Gly Gln Ser Phe Asn Ser Asn
1               5                   10

<210> SEQ ID NO 2
<211> LENGTH: 7
<212> TYPE: PRT
<213> ORGANISM: Bacillus flexus

<400> SEQUENCE: 2

Leu Ala His Gln Ala Phe Asp
1               5

<210> SEQ ID NO 3
<211> LENGTH: 9
<212> TYPE: PRT
<213> ORGANISM: Bacillus flexus

<400> SEQUENCE: 3

Leu Ser Tyr Asn Ser Thr Tyr Gly Asp
1               5

<210> SEQ ID NO 4
<211> LENGTH: 23
<212> TYPE: DNA
<213> ORGANISM: Artificial Sequence
<220> FEATURE:
<223> OTHER INFORMATION: sense primer
<220> FEATURE:
<221> NAME/KEY: modified_base
<222> LOCATION: (3)..(3)
<223> OTHER INFORMATION: I
<220> FEATURE:
```

```
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 4
gcngtnaayg gncarwsntt yaa                                             23

<210> SEQ ID NO 5
<211> LENGTH: 21
<212> TYPE: DNA
<213> ORGANISM: Artificial Sequence
<220> FEATURE:
<223> OTHER INFORMATION: antisense primer
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 5
rtcaarngcy tgrtgngcna r                                               21

<210> SEQ ID NO 6
<211> LENGTH: 1638
<212> TYPE: DNA
<213> ORGANISM: Bacillus flexus

<400> SEQUENCE: 6
atgtacaagc caattaaaaa gtttgcatca cttattgttt tgttaagttt tgttgccgct      60
ttcatattag ggccaaccaa tagccaagca gcggtaaatg acagtcgtt taactcgaat      120 tacaagacct atttaatggc accactaaag aaagtaacgg agtttactac gtgggaagct     180
tttgaaaatg accttcggaa ggcaaagcaa atgggtttt acgctgtgac agtagatttt      240
tggtggggag atatggagaa aaacggtgac cagcagttcg acttttctta tgcacagcga     300
ttcgcacagg cagctcgaaa tgcgggaata aaaatggtgc cgattatctc gacgcatcaa     360
tgtggtggaa atgtaggaga tgactgtaac acgcctcttc cttcatggat ttggaatact     420
aaaacagatg atagcctata ttttaaatca gaaacaggta cagtaaacaa agaaacagta     480
aacccattag cgacagacgt aattacaaaa cagtacgggg agctatacac agcatttgcg     540
caagcgttag caccgtataa agacgttatt ccaaaggttt atttatcagg ggaccagct     600 ggtgagcttc gctatccttc atatacagct gctgatggga caggctaccc ttctagaggg     660
aaatttcaag catacacaga ctttgcaaaa tctaaattcc aaatgtgggc cgttaacaag     720
tatggctcgt tagcgggtgt aaaccaagca tggggactaa gttaacatc aacatcacaa     780 atttttaccac cttcagatgg gaatcagttt ttaaaggatg gatataacac aaactatgga     840
```

```
aaagactttc tagaatggta tcaaggagtt ctgcaagacc atgcaaagcg tattggagca    900
ttagctcatc aagcctttga tccggtgttt aatgtgcctg taggagctaa aatagcaggg    960
atacactggc aatataataa tccaacaatg cctcatgctg ctgaaaagcc agcgggttat   1020
aataactaca gtacgttatt agactcattt aaaacagcca agctagattt gacgtttacg   1080
tgcttagaaa tggttgatag cgggacatat cctgagtatt caatgccaaa acgttagta    1140 aaagaagttg caagcctagc aaacgcaaaa gggattgtat taaatggtga aaatgcttta   1200
agtatcggaa gtgaagagca gtataaacgc gcagctgaaa tgacatttaa ctataacttt   1260
gcgggcttta cgcttttaag attctatgat gttattaata actcaacgcg tatgagccag   1320
tttaatcagc acttaaatat aaaaccggtt gcacagacaa tggttgttaa aaatgcacct   1380
acatcgtctg gagagagtgt ttcacatcgtc ggagatcgtc ctgaacttgg acagtgggac   1440
acaatcgctt atccaattaa actctcttac aactcaacgt acggagattg gagaggaacc   1500
gttaatttcc cagccgatcg aagcgttcag ttcaaagcga ttatcaagcg ctcggatggc   1560
tcattaaaat catggcaacc aacccagcag tattggaatg ttccaggaac gcctacaacg   1620
tatacgaata attggtaa                                                 1638
```

<210> SEQ ID NO 7
<211> LENGTH: 545
<212> TYPE: PRT
<213> ORGANISM: Bacillus flexus

<400> SEQUENCE: 7

```
Met Tyr Lys Pro Ile Lys Lys Phe Ala Ser Leu Ile Val Leu Leu Ser
1               5                   10                  15

Phe Val Ala Ala Phe Ile Leu Gly Pro Thr Asn Ser Gln Ala Ala Val
            20                  25                  30

Asn Gly Gln Ser Phe Asn Ser Asn Tyr Lys Thr Tyr Leu Met Ala Pro
        35                  40                  45

Leu Lys Lys Val Thr Glu Phe Thr Thr Trp Glu Ala Phe Glu Asn Asp
    50                  55                  60

Leu Arg Lys Ala Lys Gln Asn Gly Phe Tyr Ala Val Thr Val Asp Phe
65                  70                  75                  80

Trp Trp Gly Asp Met Glu Lys Asn Gly Asp Gln Gln Phe Asp Phe Ser
                85                  90                  95

Tyr Ala Gln Arg Phe Ala Gln Ala Ala Arg Asn Ala Gly Ile Lys Met
            100                 105                 110

Val Pro Ile Ile Ser Thr His Gln Cys Gly Gly Asn Val Gly Asp Asp
        115                 120                 125

Cys Asn Thr Pro Leu Pro Ser Trp Ile Trp Asn Thr Lys Thr Asp Asp
    130                 135                 140

Ser Leu Tyr Phe Lys Ser Glu Thr Gly Thr Val Asn Lys Glu Thr Val
145                 150                 155                 160

Asn Pro Leu Ala Thr Asp Val Ile Thr Lys Gln Tyr Gly Glu Leu Tyr
                165                 170                 175

Thr Ala Phe Ala Gln Ala Leu Ala Pro Tyr Lys Asp Val Ile Pro Lys
            180                 185                 190

Val Tyr Leu Ser Gly Gly Pro Ala Gly Glu Leu Arg Tyr Pro Ser Tyr
        195                 200                 205

Thr Ala Ala Asp Gly Thr Gly Tyr Pro Ser Arg Gly Lys Phe Gln Ala
    210                 215                 220
```

```
Tyr Thr Asp Phe Ala Lys Ser Lys Phe Gln Met Trp Ala Val Asn Lys
225                 230                 235                 240

Tyr Gly Ser Leu Ala Gly Val Asn Gln Ala Trp Gly Leu Ser Leu Thr
            245                 250                 255

Ser Thr Ser Gln Ile Leu Pro Pro Ser Asp Gly Asn Gln Phe Leu Lys
        260                 265                 270

Asp Gly Tyr Asn Thr Asn Tyr Gly Lys Asp Phe Leu Glu Trp Tyr Gln
    275                 280                 285

Gly Val Leu Gln Asp His Ala Lys Arg Ile Gly Ala Leu Ala His Gln
290                 295                 300

Ala Phe Asp Pro Val Phe Asn Val Pro Val Gly Ala Lys Ile Ala Gly
305                 310                 315                 320

Ile His Trp Gln Tyr Asn Asn Pro Thr Met Pro His Ala Ala Glu Lys
                325                 330                 335

Pro Ala Gly Tyr Asn Asn Tyr Ser Thr Leu Leu Asp Ser Phe Lys Thr
            340                 345                 350

Ala Lys Leu Asp Leu Thr Phe Thr Cys Leu Glu Met Val Asp Ser Gly
        355                 360                 365

Thr Tyr Pro Glu Tyr Ser Met Pro Lys Thr Leu Val Lys Glu Val Ala
370                 375                 380

Ser Leu Ala Asn Ala Lys Gly Ile Val Leu Asn Gly Glu Asn Ala Leu
385                 390                 395                 400

Ser Ile Gly Ser Glu Glu Gln Tyr Lys Arg Ala Ala Glu Met Thr Phe
                405                 410                 415

Asn Tyr Asn Phe Ala Gly Phe Thr Leu Leu Arg Phe Tyr Asp Val Ile
            420                 425                 430

Asn Asn Ser Thr Arg Met Ser Gln Phe Asn Gln His Leu Asn Ile Lys
        435                 440                 445

Pro Val Ala Gln Thr Met Val Val Lys Asn Ala Pro Thr Ser Ser Gly
450                 455                 460

Glu Ser Val Tyr Ile Val Gly Asp Arg Pro Glu Leu Gly Gln Trp Asp
465                 470                 475                 480

Thr Ile Ala Tyr Pro Ile Lys Leu Ser Tyr Asn Ser Thr Tyr Gly Asp
                485                 490                 495

Trp Arg Gly Thr Val Asn Phe Pro Ala Asp Arg Ser Val Gln Phe Lys
            500                 505                 510

Ala Ile Ile Lys Arg Ser Asp Gly Ser Leu Lys Ser Trp Gln Pro Thr
        515                 520                 525

Gln Gln Tyr Trp Asn Val Pro Gly Thr Pro Thr Thr Tyr Thr Asn Asn
530                 535                 540

Trp
545

<210> SEQ ID NO 8
<211> LENGTH: 29
<212> TYPE: DNA
<213> ORGANISM: Artificial Sequence
<220> FEATURE:
<223> OTHER INFORMATION: sense primer

<400> SEQUENCE: 8
gtactcatat ggcggtaaat ggacagtcg                                    29

<210> SEQ ID NO 9
<211> LENGTH: 29
<212> TYPE: DNA
```

```
<213> ORGANISM: Artificial Sequence
<220> FEATURE:
<223> OTHER INFORMATION: antisense primer

<400> SEQUENCE: 9
cgactctcga gttaccaatt attcgtata                                              29
```

METHOD FOR IMPROVEMENT OF FOODS UTILIZING β-AMYLASE

TECHNICAL FIELD

The present invention relates to a use of a novel β-amylase. Specifically, the invention relates to an application of the novel β-amylase derived from a microorganism to the food field. The present application claims priority based on the Japanese Patent Application No. 2009-168550 filed on Jul. 17, 2009, and the content of the patent application is incorporated by reference in its entirety.

BACKGROUND ART

Conventionally, β-amylases have been known as those derived from plants such as soybean, wheat, barley, malt, sweet potato and potato. Particularly, β-amylases which are extracted and purified from cereals such as soybean, wheat, barley, and malt have been widely industrially used for producing maltose-containing syrups used in the sugar production industry, bread-making industry, and brewing industry. Among β-amylases derived from plants, one derived from soybean has high enzyme activity and high thermostability.

By the way, the price of corn has been increased due to demand expansion of bioethanol in recent years. According to this reason, planting has been shifted from soybean and wheat to corn. Therefore, soybean, wheat, barley, and the like become scarce and prices thereof are increased, and thus, securing materials of β-amylases is in a difficult situation.

β-amylase is an enzyme that acts on polysaccharides having α-1,4 bonds of glucose as main chains, such as starch and glycogen, and digests into maltose units from non-reducing terminals. β-amylase has been known for its existence in higher plants such as soybean and wheat from a long time ago. In 1972, since existence of an enzyme showing an action mechanism that is the same as a higher plant β-amylase also in a microorganism was disclosed, many microorganisms have been found as β-amylase producing bacteria (Non-patent Document 1).

So far, bacteria belonging to Bacillus sp. such as Bacillus cereus, Bacillus polymyxa, Bacillus circulans, Bacillus megaterium and Bacillus stearothermophilus, or Streptomyces sp., Pseudomonas sp., and the like have been reported as β-amylase producing bacteria. However, many of the bacteria have low productivity and hardly attained practical applications.

On the other hand, an amylase produced from filamentous fungi such as Aspergillus sp. is an endo-type enzyme which digests amylose and amylopectin. Therefore, when the amylase is used, glucose, maltotriose, and other oligosaccharides have been also largely produced in addition to maltose. What is more, such an amylase has low thermostability and its practical use in maltose production is small.

Bacillus stearothermophilus produces a maltose-generating enzyme having high thermostability (Patent Document 1, Non-patent Document 2). This enzyme is an exo-type and generates maltose from a non-reducing terminal of starch, and the generated α-maltose. In addition, the enzyme does not exactly hydrolyze in a maltose unit as a plant-derived β-amylase dose, and it has been reported that the enzyme also generates small amounts of maltopentaose (G5) and maltohexaose (G6) in addition to maltotetraose (G4), maltotriose (G3) and maltose (G2) in an early stage of a reaction, digests Shardinger dextrin into maltose and glucose, and digests maltotriose into maltose and glucose. Accordingly, 6 to 8% of glucose is contained in a digestion product of starch by this enzyme. Therefore, the enzyme is not suitable for production of a maltose syrup with high purity.

CITATION LIST

Patent Literature
Patent Document 1: Japanese Unexamined Patent Publication (JP-A) No. 60-2185
Non Patent Literature
Non-patent Document 1: Handbook of Industrial Carbohydrate Enzymes, Kodansha Scientific Ltd., 1999
Non-patent Document 2: H. Outtrup, B. E. Norman, et al., Starch, Vol. 12, pp. 405 to 411

DISCLOSURE OF INVENTION

Technical Problem

As described above, plant-derived β-amylases being the mainstream of β-amylases currently have difficulty in stable supply. An enzyme amount obtained from plants is determined and its production amount is limited. On the other hand, on the ground that microorganism-derived β-amylases have reduced productivity or difficulty in mass culture, such β-amylases that have attained practical applications are less. Thus, an object of the present invention is to find a novel β-amylase excellent in a practical applicability and to provide a practical use thereof.

Solution to Problem

The present inventors have made intensive studies in view of the above-described problems. As a result, they found that Bacillus flexus that is Bacillus subtilis produces a β-amylase having heat resistance which is comparable with a β-amylase derived from soybean. The present inventors also succeeded in isolation and purification of the β-amylase and determination of the enzymatic chemical properties thereof. Furthermore, the present inventors succeeded in determination of the nucleotide sequence of a gene coding for the β-amylase. In addition, they confirmed that the β-amylase can be produced by using a transformant in which a vector containing the gene. On the other hand, the result of studying a use of the β-amylase showed that the β-amylase is useful in production of food materials and improvement of foods.

The present invention was accomplished according to the above-described achievement and described as follows.

[1] A method for improving a food, wherein a β-amylase derived from Bacillus flexus is acted on a food containing a polysaccharide or an oligosaccharide having an α-1,4 bond of glucose as the main chain.

[2] The method for improving a food according to [1], wherein the food is any one selected from the group consisting of bread or dough, rice cakes or rice cake sweets, and steamed rice or steamed rice processed products.

[3] The method for improving a food according to [1] or [2], wherein the β-amylase has the following enzymatic chemical properties:
(1) action: acting on α-1,4 glucoside bonds of polysaccharides and oligosaccharides to release maltose,
(2) substrate specificity: favorably acting on starch, amylose, amylopectin, glycogen, maltotetraose, maltopentaose, maltohexaose, maltoheptaose, but not acting on pullulan, dextran, cyclodextrin, maltotriose,
(3) optimum temperature: about 55° C.,
(4) optimum pH: about 8.0, (5) thermostability: stable at 55° C. or lower (pH 5.0, for 10 minutes),
(6) pH stability: stable at pH 4 to 9 (30° C., for 3 hours), and
(7) molecular weight: about 60,000 (SDS-PAGE).
[4] The method for improving a food according to [1] or [2], wherein the β-amylase comprises an amino acid sequence set forth in SEQ ID NO: 7, or an amino acid sequence equivalent to the amino acid sequence.
[5] The method for improving a food according to [4], wherein the equivalent amino acid sequence is an amino acid sequence that is 90% or more identical to the amino acid sequence set forth in SEQ ID NO: 7.
[6] The method for improving a food according to any one of [1] to [5], wherein other enzymes are acted in addition to the β-amylase.
[7] The method for improving a food according to [6], wherein the other enzymes are one or more enzymes selected from the group consisting of lipase, phospholipase, glucose oxidase, xylanase, protease, transglutaminase, protein glutaminase, a debranching enzyme, pullulanase, isoamylase, α-amylase, glucoamylase and maltogenic α-amylase.
[8] A food improved by the method for improving a food according to any one of [1] to [7].
[9] An enzyme composition, blending the β-amylase defined in any one of [3] to [5] and other enzymes.
[10] The enzyme composition according to [9], wherein the other enzymes are one or more enzymes selected from the group consisting of lipase, phospholipase, glucose oxidase, xylanase, protease, transglutaminase, protein glutaminase, a debranching enzyme, pullulanase, isoamylase, α-amylase, glucoamylase and maltogenic α-amylase.

BRIEF DESCRIPTION OF DRAWINGS

FIG. 9 is a graph showing a preventive effect of a β-amylase on retrogradation. A rice cake to which a β-amylase has been added was preserved at 25° C. (left), 15° C. (center), and 4° C. (right), and an inhibiting effect on hardening was examined.

DESCRIPTION OF EMBODIMENTS

Terms

Figure 1:
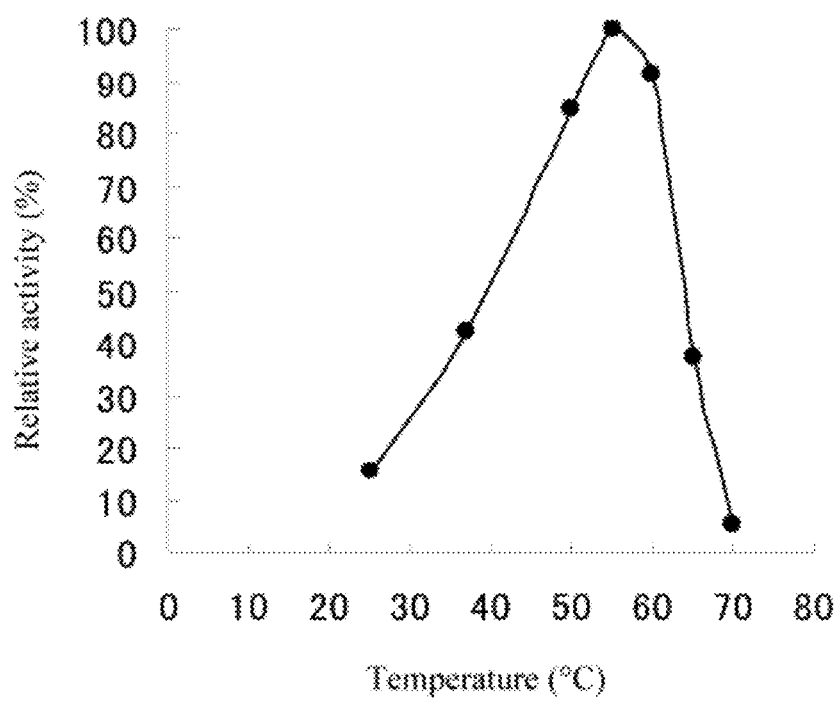
FIG. 1 is a graph showing an optimum temperature of the β-amylase derived from *Bacillus flexus*.

A "DNA coding for a protein" in the present invention refers to a DNA capable of generating the protein when it is expressed, that is, a DNA having a base sequence corresponding to the amino acid sequence of the protein. Therefore, degeneracy of a codon is also considered.

The term "isolated" in the present specification is used exchangeably with "purified". "Isolated" in the case of using in terms of the enzyme of the present invention (β-amylase) refers to, in the case that the enzyme of the present invention is derived from a natural material, a state of substantially containing no other component in the natural material except for the enzyme (substantially not containing an impure protein in particular). Specifically, for example, in the isolated enzyme of the present invention, a content of an impure protein is less than about 20% based on the whole by weight conversion, preferably less than about 10%, more preferably less than about 5%, and further more preferably less than about 1%. On the other hand, the term "isolated" in the case that the enzyme of the present invention is prepared by a genetic engineering technique refers to a state of substantially not containing other components derived from the used host cells, a culture solution, etc. Specifically, for example, in isolated enzyme of the present invention, a content of an impure protein is less than about 20% based on the whole by weight conversion, preferably less than about 10%, more preferably less than about 5%, and further more preferably less than about 1%. In addition, in the case of simply describing a "β-amylase" in the present invention, it means a "β-amylase in an isolated state" as long as a different meaning from the above meaning is clearly expressed. The term "present enzyme" used in place of the β-amylase also means the same.

"Isolated" when used for a DNA refers to typically a state of being separated from other nucleic acids that coexist in a natural state in the case that the DNA originally exists in nature. However, a part of other nucleic acid components such as a flanking nucleic acid sequence in a natural state (for example, a sequence of a promoter region and a terminator sequence) may be contained. For example, in the state of being "isolated" in the case of a genomic DNA, other DNA components that coexist in the natural state are not preferably substantially contained. On the other hand, in the state of being "isolated" in the case of a DNA prepared by a genetic engineering technique such as a cDNA molecule, cell components, a culture solution, and the like are not preferably substantially contained. In the same manner, in the state of being "isolated" in the case of a DNA prepared by a chemical synthesis, precursors (raw materials) such as dNTP, chemical substances used in the synthesis process, and the like are not preferably substantially contained. In addition, in the case of simply describing a "DNA" in the specification, it means a DNA in an isolated state as long as a different meaning from the above meaning is clearly expressed.

(β-Amylase and β-Amylase Producing Bacterium)

The first aspect of the present invention provides a β-amylase (hereinafter, also referred to as "the present enzyme") and a β-amylase producing bacterium. As shown in examples described later, results of intensive studies made by the present inventors found that *Bacillus flexus* produces a thermostable β-amylase. In addition, the inventors succeeded in separation and generation of the β-amylase and at the same time determination of its enzymatic chemical properties as shown below.

(1) Action

The present enzyme is a β-amylase, and acts on α-1,4 glucoside bonds of polysaccharides and oligosaccharides to release maltose. Glucose is hardly released.

(2) Substrate Specificity

The present enzyme is excellent in substrate specificity, and favorably acts on starch, amylose, amylopectin, glycogen, maltotetraose, maltopentaose, maltohexaose, maltoheptaose. On the other hand, the present enzyme does not act on pullulan, dextran, cyclodextrin, and maltotriose. A relative activity of 50% or more is determined to be "a substrate on which the present enzyme favorably acts", assuming that an activity in the case of using soluble starch as a substrate is the base (100%). In the same manner, a relative activity of less than 10% is determined to be "a substrate on which the present enzyme does not act". The present enzyme does not have substantial action to maltotriose and cyclodextrin (α, β, or γ). In addition, reactivity and substrate specificity of the present enzyme can be measured and evaluated in the method shown in examples described later (β-amylase activity measurement method (1)).

(3) Optimum Temperature

An optimum temperature of the present enzyme is about 55° C. The present enzyme shows high activity from about 50° C. to about 60° C. The optimum temperature is a value that was calculated in a measurement according to the β-amylase activity measurement method (in 0.1 M phosphoric acid-hydrochloric acid buffer solution (pH 5.0)), which will be described later.

(4) Optimum pH

An optimum pH of the present enzyme is about 8.0. The present enzyme shows high activity from about pH 6.0 to about 9.0. The optimum pH is determined based on a result measured in a citric acid buffer solution for the pH range from 2 to 4 and in a Britton-Robinson buffer solution for the pH range from 4 to 11, for example.

(5) Thermostability

The present enzyme shows excellent thermostability which is comparable with a β-amylase derived from soybean. The present enzyme retains 90% or more of activity even when treated under the condition at 55° C. for 10 minutes in a 0.1 M acetic acid-hydrochloric acid buffer solution (pH 5.0) containing 10 mM calcium acetate.

(6) pH Stability

The present enzyme shows a stable activity in such a wide pH range from 4 to 9. That is, if a pH of an enzyme solution subjected to a treatment is within the range, the enzyme shows 70% or more of the maximum activity after the treatment at 30° C. for 3 hours. The optimum pH is determined based on a result measured in a citric acid buffer solution for the pH range from 2 to 4 and in a Britton-Robinson buffer solution for the pH range from 4 to 11, for example.

(7) Molecular weight

The molecular weight of the present enzyme is about 60,000 (in SDS-PAGE).

The present enzyme is preferably a β-amylase derived from *Bacillus flexus*. Herein, the "β-amylase derived from *Bacillus flexus*" means a β-amylase produced by a microorganism (may be a wild-type or mutant) which is classified into *Bacillus flexus*, or a β-amylase obtained by a genetic engineering technique using β-amylase gene of *Bacillus flexus* (may be a wild-type or mutant). Therefore, a recombinant that is produced by a host microorganism introduced with β-amylase gene obtained from *Bacillus flexus* (or gene obtained by altering gene) also falls into the "β-amylase derived from *Bacillus flexus*".

*Bacillus flexus* from which the present enzyme is derived is referred to as a producing bacterium of the present enzyme for the sake of simplicity of explanation. Examples of producing bacteria of the present enzyme include *Bacillus flexus* DSM1316 (DSMZ, Germany), DSM1320 (DSMZ, Germany), DSM1667 (DSMZ, Germany), and APC9451, which will be described in examples later. In addition, the APC9451 strain has been deposited in an appointed depositary institution as described below and is easily available.

NITE Depositary institution: Patent Microorganisms Depositary, Biotechnology Development Center (2-5-8 Kazusakamatari, Kisarazu-shi, Chiba, 292-0818, Japan)

Date of deposit (date received): Apr. 9, 2008

Accession number: NITE BP-548

As described above, details of the properties of the present enzyme that has been succeeded in acquisition were clarified. The results revealed that the present enzyme shows excellent thermostability and substrate specificity. Therefore, the present enzyme is suitable for uses in food processing and glycosylation.

As a result of further studies by the present inventors, the amino acid sequence (SEQ ID NO: 7) of the β-amylase produced by *Bacillus flexus* was determined. Thus, one embodiment of the present invention is characterized by containing a protein having the amino acid sequence of SEQ ID NO: 7. Herein, in general, when a part of an amino acid sequence of a protein is altered, the protein after alteration may have equivalent functions to the protein before alteration. That is, alteration of the amino acid sequence does not give a substantial influence on functions of the protein, and the protein functions may be kept before and after the alteration. Thus, another embodiment of the present invention provides a protein containing an amino acid sequence equivalent to the amino acid sequence set forth in SEQ ID NO: 7 and having a β-amylase activity (hereinafter, also referred to as "an equivalent protein"). The "equivalent amino acid sequence" herein refers to an amino acid sequence having partial difference from the amino acid sequence set forth in SEQ ID NO: 7, in which the difference however does not give substantial influence on the protein functions (means a β-amylase activity herein). "Having a β-amylase activity" means that acting on polysaccharides and oligosaccharides having α-1,4 bonds of glucose as main chains, such as starch and glycogen, to digest into maltose units from non-reducing terminals, and a degree of the activity is not particularly limited as long as functions of a β-amylase can be exhibited. However, the activity is preferably in the same level or higher than an activity of a protein containing the amino acid sequence set forth in SEQ ID NO: 7.

The "partial difference of an amino acid sequence" typically means occurrence of mutation (change) in an amino acid sequence by deletion or substitution of one to several amino acids constituting the amino acid sequence, or addition or insertion of one to several amino acids, or combination thereof. The difference of an amino acid sequence herein is acceptable as long as a β-amylase activity is retained (some fluctuation in the activity may occur). As long as this condition is satisfied, a position at which an amino acid sequence is different is not particularly limited, and difference may be generated in a plurality of positions. Plurality herein is, for example, the number that corresponds to less than about 30% of the entire amino acids, preferably the number that corresponds to less than about 20%, more preferably the number that corresponds to less than about 10%, further more preferably the number that corresponds to less than about 5%, and the most preferably the number that corresponds to less than about 1%. That is, an equivalent protein has an identity of, for example, about 70% or more to the amino acid sequence set forth in SEQ ID NO: 7, preferably about 80% or more, more preferable about 90% or more, further more preferably about 95% or more, and the most preferably about 99% or more.

It is preferable that an equivalent protein is obtained by generating preservative amino acid substitution in an amino acid residue that is not essential to a β-amylase activity. The "preservative amino acid substitution" herein refers to substituting an amino acid residue into an amino acid residue having a side chain with similar properties. Amino acid residues are classified into several families according to their side chains, such as basic side chains (e.g., lysine, arginine, and histidine), acidic side chains (e.g., aspartic acid and glutamic acid), uncharged polar side chains (e.g., glycine, asparagines, glutamine, serine, threonine, tyrosine, and cysteine), nonpolar side chains (e.g., alanine, valine, leucine, isoleucine, proline, phenylalanine, methionine, and tryptophan), β-branched side chains (e.g., threonine, valine, and isoleucine), and aromatic side chains (e.g., tyrosine, phenylalanine, tryptophan, and histidine). Preservative amino acid substitution is preferably substitution among amino acid residues in the same family.

"An equivalent protein" may have additional properties. Examples of such properties include a property of having excellent stability as compared to a protein composed of the amino acid sequence set forth in SEQ ID NO: 7, a property of exhibiting a different function only at a low temperature and/or a high temperature, and a property of having a different optimum pH.

By the way, an identity (%) of two amino acid sequences or two nucleic acids (hereinafter, "two sequences" is used as the term including them) can be determined by the following procedure, for example. Firstly, two sequences are aligned so that the sequences can be optimally compared (for example, a gap is introduced in the first sequence and an alignment with the second sequence may be optimized). When a molecule (amino acid residue or nucleotide) at a specific position in the first sequence is the same as a molecule at a position corresponded in the second sequence, the molecules in these positions can be the same. An identity of two sequences is a function of the number of identical positions that are common in the two sequences (i.e., identity (%)=the number of identical positions/the total number of positions×100), and the number and sizes of gaps required for optimization of the alignment are also preferably taken into consideration. Comparison of two sequences and determination of identity thereof are feasible using a mathematical algorithm. A specific example of a mathematical algorithm applicable to comparison of sequences includes algorithm described in Karlin and Altschul (1990) Proc. Natl. Acad. Sci. USA 87: 2264-68 and modified in Karlin and Altschul (1993) Proc. Natl. Acad. Sci. USA 90: 5873-77, but is not limited thereto. Such an algorithm is incorporated into the NBLAST program and XBLAST program (version 2.0) described in Altschul et al. (1990) J. Mol. Biol. 215:403-10. In order to obtain an equivalent nucleotide sequence to the nucleic acid molecule of the present invention, for example, BLAST nucleotide search may be carried out by the NBLAST program setting score=100 and wordlength=12. In order to obtain an equivalent amino acid sequence to the polypeptide molecule of the present invention, for example, BLAST polypeptide search may be carried out by the XBLAST program setting score=50 and wordlength=3. In order to obtain a gap alignment for comparison, Gapped BLAST described in Altschul et al. (1997) Amino Acids Research 25(17): 3389-3402 is available. When BLAST and Gapped BLAST are utilized, a default parameter of a corresponded program (e.g., XBLAST and NBLAST) can be used. See http://www.ncbi.nlm.nih.gov for detail. An example of another mathematical algorithm applicable to comparison of sequences includes the algorithm described in Myers and Miller (1988) Comput Appl Biosci. 4:11-17. Such an algorithm is incorporated in the ALIGN program available from, for example, the GENESTREAM network server (IGH Montpellier, France) or the ISREC server. When the ALIGN program is used for comparison of amino acid sequences, for example, the PAM120 residue mass table is used setting gap length penalty=12 and gap penalty=4.

An identity of two amino acid sequences can be determined with the GAP program of the GCG software package using Blossom 62 matrix or PAM250 matrix, and setting gap weight=12, 10, 8, 6 or 4 and gap length weight=2, 3 or 4. Further, a homology of two nucleic acid sequences can be determined with the GAP program of the GCG software package (available from http://www.gcg.com) setting gap weight=50 and gap length weight=3.

The present enzyme may be a part of a larger protein (e.g., fusion protein). Examples of sequences added in a fusion protein include a sequence that functions for purification, such as a multiple histidine residue, and an additive sequence that secures stability in recombinant production.

The present enzyme having the above-described amino acid sequence can be easily prepared in a genetic engineering technique. For example, a suitable host cell (e.g., *E. coli*) is transformed with a DNA coding for the present enzyme and a protein expressed in the transformant is recovered to thus prepare the present enzyme. The recovered protein is suitably purified according to the intended use. Various modifications are possible when the present enzyme is obtained as a recombinant protein as described above. For example, when a DNA coding for the present enzyme and another suitable DNA are inserted into the same vector to produce a recombinant protein using the vector, the present enzyme containing the recombinant protein linked to a desired peptide or protein. Furthermore, addition of a sugar chain and/or lipid, or modification that generates processing of N-terminal or C-terminal may be preformed. The above modifications enable extraction of a recombinant protein, simplification of purification, addition of biological functions, or the like.

(DNA Coding for β-Amylase)

The second aspect of the present invention provides a gene coding for the present enzyme, that is, novel β-amylase gene. Gene of the invention in one embodiment consist of a DNA coding for an amino acid sequence set forth in SEQ ID NO: 7. A specific example of the embodiment is a DNA which consists of a base sequence set forth in SEQ ID NO: 6.

By the way, in general, when a part of DNA coding for a protein is altered, the protein coded by the DNA after alteration may have equivalent functions to the protein coded by the DNA before alteration. That is, alteration of the DNA sequence does not give a substantial influence on functions of the protein to be coded, and the functions of the protein to be coded may be kept before and after the alteration. Thus, another embodiment of the present invention provides a DNA coding for a protein containing a base sequence equivalent to the base sequence set forth in SEQ ID NO: 6 and having a β-amylase activity (hereinafter, also referred to as "an equivalent DNA"). The "equivalent base sequence" herein refers to a base sequence having partial difference from a nucleic acid set forth in SEQ ID NO: 6, wherein the difference however gives no substantial influence on functions of a protein coded thereby (means a (3-amylase activity herein).

A specific example of the equivalent DNA is a DNA that hybridizes to a base sequence complementary to the base sequence set forth in SEQ ID NO: 6 under stringent conditions. The "stringent conditions" herein refer to conditions wherein a so-called specific hybrid is formed and a nonspecific hybrid is not formed. Such stringent conditions are known by a person skilled in the art and can be set with reference to, for example, Molecular Cloning (Third Edition, Cold Spring Harbor Laboratory Press, New York) and Current protocols in molecular biology (edited by Frederick M. Ausubel et al., 1987). Examples of the stringent conditions include conditions of using a hybridization solution (50% formamide, 10×SSC (0.15 M NaCl, 15 mM sodium citrate, pH 7.0), a 5×Denhardt solution, 1% SDS, 10% dextran sulfate, 10 μg/ml of denatured salmon sperm DNA, and a 50 mM phosphate buffer (pH7.5)) and incubating at about 42° C. to about 50° C., thereafter washing with 0.1×SSC and 0.1% SDS at about 65° C. to about 70° C. Examples of more preferable stringent conditions include conditions of using 50% formamide, 5×SSC (0.15 M NaCl, 15 mM sodium citrate, pH 7.0), 1×Denhardt solution, 1% SDS, 10% dextran sulfate, 10 μg/ml of denatured salmon sperm DNA, and a 50 mM phosphate buffer (pH 7.5) as a hybridization solution.

Other specific examples of an equivalent DNA include a DNA composed of a base sequence containing substitution, deletion, insertion, addition, or inversion of one or plural bases with reference to the base sequence set forth in SEQ ID NO: 6, and coding for a protein that has a β-amylase activity. Substitution and deletion of bases may occur in a plurality of sites. "Plurality" herein indicates, for example, 2 to 40 bases, preferably 2 to 20 bases, and more preferably 2 to 10 bases although depending on a position and a type of an amino acid residue in a steric structure of a protein coded by the DNA. Such an equivalent DNA as described above can be obtained by altering a DNA having the base sequence set forth in SEQ ID NO: 6 so as to contain substitution, deletion, insertion, addition and/or inversion of bases, utilizing introduction of variation, for example, a restriction enzyme treatment, a treatment with exonuclease, DNA ligase, or the like, a site-directed mutagenesis method (Molecular Cloning, Third Edition, Chapter 13, Cold Spring Harbor Laboratory Press, New York), or a random mutagenesis method (Molecular Cloning, Third Edition, Chapter 13, Cold Spring Harbor Laboratory Press, New York). An equivalent DNA can be also obtained by other methods such as exposure to ultraviolet radiation.

Other examples of an equivalent DNA include a DNA in which for such a difference in bases as described above is found due to a polymorphism typically represented by SNP (monobasic polymorphism).

Gene of the present invention can be prepared into a state of being isolated by use of a standard genetic engineering technique, molecular biological technique, biochemical technique, or the like, with reference to sequence information disclosed in the specification or attached sequence listing. Specifically, the DNA can be prepared by suitably using an oligonucleotide probe primer capable of hybridizing specifically to gene of the present invention from a suitable genomic DNA library or cDNA library of *Bacillus flexus*, or an extraction solution of *Bacillus flexus* bacterial cells. An oligonucleotide probe primer can be easily synthesized using a commercially available automation DNA synthesizer, or the like. For a production method of a library used to prepare gene of the present invention, for example, Molecular Cloning, Third Edition, Cold Spring Harbor Laboratory Press, New York can be referred.

For example, gene having the base sequence set forth in SEQ ID NO: 6 can be isolated by use of a hybridization method in which the whole or a part of the base sequence or its complementary sequence is used as a probe. Furthermore, gene can be amplified and isolated by use of a nucleic acid amplification reaction (for example, PCR) using a synthesized oligonucleotide primer designed so as to hybridize specifically to a part of the base sequence. Desired gene can be also obtained by chemical synthesis based on information of the amino acid sequence set forth in SEQ ID NO: 7 and the base sequence set forth in SEQ ID NO: 6 (reference document: Gene, 60(1), 115-127 (1987)).

Specific example of a method of obtaining gene of the present invention will be shown below. Firstly, the present enzyme (β-amylase) is isolated and purified from *Bacillus flexus* to obtain information about a partial amino acid sequence thereof. For a determination method of the partial amino acid sequence, for example, a purified β-amylase is directly subjected to an amino acid sequence analysis [protein sequencer 476A, manufactured by Applied Biosystems, Inc., etc.] in the Edman degradation method [Journal of Biological Chemistry, Vol. 256, pp. 7990 to 7997 (1981)] according to a common method. It is effective that a limited proteolysis is performed by the action of a proteolytic enzyme to separate and purify the obtained peptide fragment and an amino acid sequence analysis is carried out on the obtained purified peptide fragment.

β-amylase gene is cloned based on the information of the partial amino acid sequence thus obtained. For example, cloning can be performed using a hybridization method or PCR. When a hybridization method is used, for example, a method described in Molecular Cloning (Third Edition, Cold Spring Harbor Laboratory Press, New York) can be used.

When a PCR method is used, the following method can be used. Firstly, a PCR reaction is performed with a synthesized oligonucleotide primer that is designed based on the information of the partial amino acid sequence, using a genomic DNA of a microorganism that produces a β-amylase as a template to thus obtain directed gene fragment. The PCR method is carried out according to a method described in PCR Technology [PCR Technology, edited by Erlich H A, Stocktonpress Co.), issued in 1989]. Furthermore, the base sequence is determined for this amplified DNA fragment in a generally used method, for example, the dideoxy chain termination method, to determine a sequence that corresponds to a partial amino acid sequence of a β-amylase in the determined sequence other than the sequence of the synthesized oligonucleotide primer and a part of desired β-amylase gene can be obtained. A hybridization method, etc. is further performed using obtained gene fragment as a probe, which enables a gene coding for the full length of the β-amylase to be cloned.

In Examples described later, a sequence of a gene coding for a β-amylase produced by *Bacillus flexus* was determined using the PCR method. The whole base sequence of the gene coding for a β-amylase derived from *Bacillus flexus* is set forth in SEQ ID NO: 6. An amino acid sequence coded by the base sequence is determined (SEQ ID NO: 7). In addition, a base sequence that corresponds to the amino acid sequence set forth in SEQ ID NO: 7 exists in the plural number except for the base sequence set forth in SEQ ID NO: 6.

The whole or a part of β-amylase gene (SEQ ID NO: 6) in which the whole base sequence has been revealed is used as a probe for hybridization, thereby enabling selection of a DNA having high homology to β-amylase gene set forth in SEQ ID NO: 6 from a genomic DNA library or a cDNA library of another β-amylase producing microorganism.

A primer for PCR can be designed in the same manner. A PCR reaction is performed using this primer to thus detect a gene fragment having high homology to above-described β-amylase gene and the whole gene can be also obtained.

A protein coded by the gene is produced and the β-amylase activity is measured, and it can be thus confirmed whether gene is a gene coding for a protein having a β-amylase activity or not. In addition, the base sequence of the obtained gene (or an amino acid sequence coded by gene) is compared to the base sequence of above-described β-amylase gene (or an amino acid sequence coded by gene) to thus examine a gene structure and homology and it may be determined whether the gene codes for a protein having a β-amylase activity or not.

Since the primary structure and the gene structure were clarified, an altered β-amylase (gene subjected to at least one of deletion, addition, insertion and substitution of one or plural amino acid residues) can be obtained by introduction of random mutation or site-directed mutation. Accordingly, a gene coding for a β-amylase that has a β-amylase activity but is different in properties such as an optimum temperature, a stable temperature, an optimum pH, a stable pH, and substrate specificity. Furthermore, an altered β-amylase can be produced in genetic engineering.

Herein, a plan for mutagenesis is implemented, for example, by referring to a characteristic sequence on a gene sequence. The characteristic sequence can be referred, for example, by considering prediction of steric structure of the protein and homology to a known protein.

As a method of introducing random mutation is exemplified, an example of a method of chemically treating a DNA includes a method in which sodium hydrogen sulfite is acted to cause transition mutation that transforms a cytosine base to an uracil base [Proceedings of the National Academy of Sciences of the USA, Vol. 79, pp. 1408 to 1412 (1982)], an example of a biochemical method includes a method of generating a base substitution in a process of synthesizing a duplex in the presence of [α-S] dNTP [Gene, Vol. 64, pp. 313 to 319 (1988)], and an example of a method of using PCR includes a method in which PCR is performed adding manganese to a reaction system to reduce accuracy of nucleotide intake [Analytical Biochemistry, Vol. 224, pp. 347 to 353 (1995)].

As a method of introducing site-directed mutation is exemplified, examples include a method of using amber mutation, gapped duplex method, Nucleic Acids Research, Vol. 12, No. 24, pp. 9441 to 9456 (1984)], a method of using a recognition site of a restricted enzyme [Analytical Biochemistry, Vol. 200, pp. 81 to 88 (1992), Gene, Vol. 102, pp. 67 to 70 (1991)], a method of using mutation of dut (dUTPase) and ung (uracil DNA glycosylase) mutation [Kunkel method, Proceedings of the National Academy of Sciences of the USA, Vol. 82, pp. 488 to 492 (1985)], a method of using amber mutation with a DNA polymerase and a DNA ligase [Oligonucleotide-directed Dual Amber: ODA method, Gene, Vol. 152, pp. 271 to 275 (1995), JP-A No. 7-289262], a method of using a host that induces a DNA restoration system (JP-A No. 8-70874), a method of using a protein that catalyzes a DNA chain exchange reaction (JP-A No. 8-140685), a method by PCR using two types of primers for mutagenesis to which recognition sites of a restricted enzyme are added (U.S. Pat. No. 5,512,463), a method by PCR using a duplex DNA vector having inactivated chemical resistant gene and two types of primers [Gene, Vol. 103, pp. 73 to 77 (1991)], and a method by PCR using amber mutation [International Publication of WO98/02535].

A use of a commercially available kit also makes it possible to easily introduce site-directed mutation. Commercially available kits that can be used include, for example, Mutan (registered trademark)-G (manufactured by TAKARA SHUZO CO., LTD.) using the gapped duplex method, Mutan (registered trademark)-K (manufactured by TAKARA SHUZO CO., LTD.) using the Kunkel method, and Mutan (registered trademark)-Express Km (manufactured by TAKARA SHUZO CO., LTD.) using the ODA method, a QuikChange™ Site-Directed Mutagenesis Kit [manufactured by STRATAGENE Co.] using a primer for mutagenesis and a *Pyrococcus furiosus*-derived DNA polymerase, and for a kit that can use a PCR method, TaKaRa LA PCR in vitro Mutagenesis Kit (manufactured by TAKARA SHUZO CO., LTD.), Mutan (registered trademark)-Super Express Km (manufactured by TAKARA SHUZO CO., LTD.), and the like can be used.

As described above, the primary structure and the gene structure of the β-amylase were provided according to the present invention, which thus enables genetically engineered production of a protein having a β-amylase activity with high purity, at a low cost.

(Recombinant Vector)

A further aspect of the present invention relates to a recombinant vector containing gene of the present invention. The term "vector" in the present specification refers to a nucleic acid molecule that can transfer a nucleic acid molecule inserted in the vector into a target such as a cell, and its type and form are not particularly limited. Therefore, the vector of the present invention can be a form of a plasmid vector, a cosmid vector, a phage vector, and virus vectors (such as an adenovirus vector, an adeno-associated virus vector, a retrovirus vector, a herpesvirus vector).

A suitable vector is selected according to its intended use (cloning, expression of a protein) and in consideration of a type of a host cell. Specific examples of a vector include a vector whose host is *E. coli* (such as M13 phage or an altered form thereof, λ, phage or an altered form thereof, pBR322 or an altered form thereof (e.g., pB325, pAT153, pUC8)), a vector whose host is a yeast (e.g., pYepSec1, pMFa, and pYES2), a vector whose host is insect cell (e.g., pAc and pVL), and a vector whose host is a mammal cell (e.g., pCDM8 and pMT2PC).

The recombinant vector of the present invention is preferably an expression vector.

The "expression vector" refers to a vector capable of introducing a nucleic acid inserted in the expression vector into a target cell (host cell) and expressing it in the cell. The expression vector generally contains a promoter sequence that is necessary for expression of a nucleic acid inserted, an enhancer sequence that promotes expression, and the like. An expression vector containing a selection marker can also be used. When such an expression vector is used, whether the expression vector has been introduced or not (and the degree of introduction) can be confirmed using the selection marker.

Insertion of gene of the present invention into a vector, insertion of selection marker gene (if necessary), insertion of a promoter (if necessary), and the like can be performed in a standard recombinant DNA technique (for example, a known method of using a restricted enzyme and a DNA ligase, which can be referred in Molecular Cloning, Third Edition, 1.84, Cold Spring Harbor Laboratory Press, New York).

(Transformant)

The present invention further relates to a transformant in which a gene of the present invention has been introduced. In the transformant of the present invention, gene of the invention is present as a foreign molecule. The transformant of the present invention is preferably prepared by transfection or transformation using the above-described vector of the invention. Transfection or transformation can be performed by calcium phosphate co-sedimentation, electroporation (Potter, H. et al., Proc. Natl. Acad. Sci. U.S.A. 81, 7161-7165 (1984)), lipofection (Feigner, P. L. et al., Proc. Natl. Acad. Sci. U.S.A.

84, 7413-7417 (1984)), microinjection (Graessmann, M. & Graessmann, A., Proc. Natl. Acad. Sci. U.S.A. 73, 366-370 (1976)), the Hanahan method (Hanahan, D., J. Mol. Biol. 166, 557-580 (1983)), the lithium acetate method (Schiestl, R. H. et al., Curr. Genet. 16, 339-346 (1989)), the protoplast-polyethylene glycol method (Yelton, M. M. et al., Proc. Natl. Acad. Sci. 81, 1470-1474 (1984)), or the like.

For a host cell, microorganisms, animal cells, plant cells, and the like can be used. Examples of microorganisms include bacteria such as *E. coli, Bacillus* sp., *Streptomyces* sp. and *Lactococcus* sp., yeasts such as *Saccharomyces* sp., *Pichia* sp. and *Kluyveromyces* sp., and filamentous fungi such as *Aspergillus* sp., *Penicillium* sp. and *Trichoderma* sp. An example of animal cells includes Baculovirus strains.

(Production Method of β-Amylase)

A further aspect of the present invention provides a method of producing a β-amylase. In one embodiment of the production method of the present invention, a step of culturing *Bacillus flexus* which is capable of producing the present enzyme (β-amylase) (step (1)) and a step of recovering the β-amylase from a culture solution and/or bacterial cells after culturing (step (2)) are carried out.

For *Bacillus flexus* in the step (1), for example, the above-described *Bacillus flexus* DSM1316, DSM1320, DSM1667, APC9451, and the like can be used. A culture method and culture conditions are not particularly limited as long as a desired enzyme is produced. That is, on condition that the present enzyme is produced, a method and culture conditions, which are suitable for culture of a microorganism used, can be appropriately employed. Either liquid culture or solid culture may be used for a culture method, and liquid culture is preferably used. In the following, liquid culture is exemplified to describe the culture conditions.

As a medium, any medium may be used as long as it is a medium capable of growing a microorganism used. Examples of medium including those containing carbon sources such as glucose, sucrose, gentiobiose, soluble starch, glycerin, dextrin, blackstrap, and organic acids, in addition, ammonium sulfate, ammonium carbonate, ammonium phosphate, ammonium acetate, or nitrogen sources such as peptone, yeast extract, corn steep liquor, casein hydrolysate, bran, and meat extracts, and furthermore, substances added with inorganic salts such as potassium salt, magnesium salt, sodium salt, phosphate salt, manganese salt, iron salt, and zinc salt can be used. Vitamins, amino acid, and the like may be added to a medium in order to promote growth of a microorganism used. The pH of the medium is adjusted to, for example, about 3 to 10, and preferably about 7 to 8, and the microorganism is cultured in an aerobic condition at a culture temperature of generally about 10 to 50° C., and preferably about 20 to 37° C., for 1 to 7 days, and preferably for 3 to 4 days. As a culture method, examples such as shake culture method, aerobic deep culture method with a Jar fermentor can be used.

Followed by the culturing under the above conditions, β-amylase is recovered from a culture solution and/or bacterial cells (step (2)). When the β-amylase is recovered from the culture solution, for example, the culture supernatant is subjected to filtration or centrifugation to remove insoluble matters, and then, separation and purification are performed through an appropriate combination of concentration using an ultrafiltration membrane, salting out such as ammonium sulfate precipitation, dialysis, various chromatography procedures such as ion exchange resin chromatography, and the like to thus obtain the present enzyme.

On the other hand, in the case of recovering from bacterial cells, for example, the bacterial cells are crushed by pressurization or ultrasonification and then subjected to separation and purification in the same manner as described above to thus obtain the present enzyme. In addition, the above-described series of steps (crushing of bacterial cells, separation, and purification) may be performed after recovering the bacterial cells from a culture solution previously by filtration, centrifugation, and the like.

In addition, confirmation of expression and identification of the expressed product can be readily achieved using an antibody against a β-amylase, and expression can be also confirmed by measuring a β-amylase activity.

In another embodiment of the present invention, β-amylase is produced using the above-described transformant. In the production method in this embodiment, firstly, the above-described transformant is cultured under the condition suitable for producing a protein coded by the gene which has been introduced to the transformant (step (i)). Culture conditions of the transformant for various vector-host systems are known and a person skilled in the art can easily employ suitable culture conditions. Followed by the culture step, a produced protein (that is, β-amylase) is recovered (step (ii)). Recovery and purification after recovery may be performed in the same manner as in the above-described embodiment. A degree of purification of the present enzyme is not particularly limited. Further, the final form of the enzyme may be a liquid or a solid (including powder).

(Enzyme Composition)

The enzyme of the present invention is provided, for example, in a form of an enzyme composition (enzyme preparation). The enzyme composition may contain vehicles, buffers, suspensions, stabilizers, preservatives, antiseptics, and physiological serine, in addition to an active ingredient (the enzyme of the present invention). As a vehicle, lactose, sorbitol, D-mannitol, sucrose, or the like can be used. As a buffer, phosphate, citrate, acetate, or the like can be used. As a stabilizer, propylene glycol, ascorbic acid, or the like can be used. As a preservative, phenol, benzalkonium chloride, benzyl alcohol, chlorobutanol, methylparaben, or the like can be used. As an antiseptic, benzalkonium chloride, paraoxybenzoic acid, chlorobutanol, or the like can be used.

In one embodiment of the enzyme composition of the present invention, other enzymes are contained as active ingredients in addition to the enzyme of the present invention (β-amylase derived from *Bacillus flexus*). Thereby, an enzyme composition capable of a multiple enzymatic reaction is formed. Examples of the "other enzymes" include lipase, phospholipase, glucose oxidase, xylanase, protease, transglutaminase, protein glutaminase, a debranching enzyme, pullulanase, isoamylase, α-amylase, glucoamylase, and maltogenic α-amylase. An example of the debranching enzyme includes Kleistase PL45 (manufactured by Daiwa Fine Chemicals Co., Ltd.), an example of the pullulanase includes Pullulanase "Amano" 3 (manufactured by Amano Enzyme Inc.), an example of the isoamylase includes an enzyme derived from *Pseudomonas amyloderamosa*, examples of the α-amylase include Kleistase P8 (manufactured by Daiwa Fine Chemicals Co., Ltd.) and Biozyme L (manufactured by Amano Enzyme Inc.), an example of the glucoamylase includes Gluczyme AF6 (manufactured by Amano Enzyme Inc.), and an example of the maltogenic α-amylase includes an enzyme derived from *Geobacillus stearothermophilus*. In addition, two or more enzymes may be adopted as the "other enzymes".

(Uses of β-Amylase)

Another aspect of the present invention provides a method for generating maltose as a use of a β-amylase derived from *Bacillus flexus*. In the generation method of maltose of the invention, a β-amylase derived from *Bacillus flexus* is acted on a substrate containing a polysaccharide or an oligosaccharide having an α-1,4 bond of glucose as the main chain. Examples of the substrate include soluble starch, potato starch, cornstarch, amylopectin, glycogen, and maltooligosaccharide. A purity of the substrate is not particularly limited. Accordingly, a β-amylase may be acted on a substrate in a state of being mixed with other substances. Alternatively, a β-amylase may be acted on two or more substrates at the same time.

The generation method of maltose of the invention is characterized by using a β-amylase derived from *Bacillus flexus*, and preferably uses the above-described β-amylase of the present invention (the present enzyme) as the β-amylase. The generation method of maltose of the invention is used in, for example, production of a maltose-containing syrup and a maltose starch syrup.

A further aspect of the present invention provides a method of using a β-amylase derived from *Bacillus flexus* for improving agents of bread and dough, antioxidants of rice cakes and rice cake sweets, antioxidants of steamed rice, or the like. Such a method of changing characteristics of a food is referred to "a method for improving a food" in the present invention. A food to be improved by the method for improving a food of the present invention is a food containing a polysaccharide or an oligosaccharide having a α-1,4 bond of glucose as the main chain. A food is not limited as long as this condition is satisfied. Examples of a food to be improved by the present invention include bread or dough, rice cakes or rice cake sweets, and steamed rice. The "bread or dough" in the present invention refers to general dough, rice cakes, steamed bread dough, donut dough, pastry dough, pizza crusts, hot cake dough, sponge cake dough, crape dough, Chinese dumpling dough, and the like, which are obtained by adding water, etc. to flour as the principle material, and further adding raw materials such as fats, saccharides, dairy products, eggs, yeast foods, various enzymes, and various emulsifiers according to necessity, and then undergoing a kneading step regardless of presence or absence of addition of yeasts, and products obtained by shaping, heating such dough, and so on (such as baking in an oven, an iron pot, etc., steaming and frying in oil) (such as bread, donuts, pastries, pizzas, hot cakes, sponge cakes, crapes, and Chinese dumplings). The "bread or dough" also includes dough and products obtained by mixing cereals other than flour, for example, rye.

The "rice cakes or rice cake sweets" in the present invention refers to plate rice cakes, daifukumochi, kashiwamochi, kusamochi, sakuramochi, rice dumplings, suama, uiro, rice flour dumplings, gyuhimochi, karukan manju, jouyou manju, and the like, which are obtained by using rice or rice powder as the principle material, adding water thereto, further adding raw materials such as saccharides according to necessity, and mixing these materials, and products obtained by steaming the rice cake dough. In addition, the "rice or rice powder" herein includes nonglutinous rice and glutinous rice, or rice powder and coarse rice powder obtained by washing nonglutinous rice with water, drying and crushing, and rice cake powder obtained by washing glutinous rice with water, drying and milling. The "rice or rice powder" further includes starch that constitutes rice or rice powder.

The "steamed rice or steamed rice processed food" in the present invention refers to products obtained by steaming rice and products obtained by processing steamed rice. The rice used herein refers to general rice such as rice, glutinous rice, and brown rice. These ingredients may be used solely or plural types may be mixed, and other cereals may be further mixed. Steamed rice added with seasonings and flavors in a steaming stage (e.g., red-bean rice, seasoned steamed rice and rice porridge) and steamed rice added with seasonings and flavors (e.g., risotto and rice porridge), or various foods using steamed rice (e.g., rice ball, sushi, packed lunch, and rice noodle), and the like also falls into the "steamed rice or steamed rice processed products".

In the improvement method of the present invention, a β-amylase derived from *Bacillus flexus* is acted on foods as described above. Timing for acting a β-amylase is not particularly limited, and in general, the β-amylase is added to raw materials to be mixed or the β-amylase is added to a food during production or processing, thereby acting the enzyme. An adding amount of the β-amylase differs depending on a food to be improved, a degree of improvement, etc., and for example, the adding amount is 2 U to 40 U per 100 g of a food. In addition, an activity value herein is defined according to the β-amylase activity measurement method (2) that will be described later.

In the maltose generation method and the method for improving a food such as bread, rice cakes and steamed rice in the present invention, other enzymes can be also used in combination with a β-amylase. For the "other enzymes", an enzyme that acts on a polysaccharide or an oligosaccharide having an α-1,4 bond of glucose as the main chain can be used. Examples of the enzymes include a debranching enzyme, pullulanase, isoamylase, α-amylase, glucoamylase, and maltogenic α-amylase. An example of the debranching enzyme includes Kleistase PL45 (manufactured by Daiwa Fine Chemicals Co., Ltd.), an example of the pullulanase includes pullulanase "Amano" 3 (manufactured by Amano Enzyme Inc.), an example of the isoamylase includes an enzyme derived from *Pseudomonas amyloderamosa*, examples of the α-amylase include Kleistase P8 (manufactured by Daiwa Fine Chemicals Co., Ltd.) and Biozyme L (manufactured by Amano Enzyme Inc.), an example of the glucoamylase includes Gluczyme AF6 (manufactured by Amano Enzyme Inc.), and an example of the maltogenic α-amylase includes an enzyme derived from *Geobacillus stearothermophilus*. In the method for improving a food such as bread, rice cakes and steamed rice, lipase, phospholipase, glucose oxidase, xylanase, protease, transglutaminase, protein glutaminase, and the like can be also used for the "other enzymes". In addition, two or more enzymes may be adopted for the "other enzymes".

Typically, a β-amylase and the "other enzymes" are acted at the same time. However, after acting the β-amylase, the "other enzymes" may be acted, or the both may be acted in the inverse order.

EXAMPLES

β-Amylase Activity Measurement Method (1)

A β-amylase activity was measured as follows. That is, 0.5 ml of an enzyme solution was added to 0.5 ml of 0.1 M phosphoric acid-hydrochloric acid buffer solution (pH 5.0) containing 1% soluble starch and 10 mM calcium acetate, and the mixture was incubated at 37° C. for 30 minutes, thereafter adding 2.5 ml of a DNS solution (0.2% DNS, 80 mM NaOH, 0.2 M potassium sodium tartrate tetrahydrate) to terminate the reaction. After termination of the reaction, the reaction mixture was boiled for 5 minutes, and an absorbance at a wavelength of 530 nm was measured. An enzyme amount when the absorbance at a wavelength of 530 nm is 1 is assumed to be 1 unit (U).

1. Confirmation of β-Amylase Derived from *Bacillus flexus*

Four strains of *Bacillus flexus* DSM1316, DSM1320, DSM1667, and APC9451 were subjected to shaking culture at 30° C. for 3 days using liquid media having compositions shown in Table 1.

TABLE 1

| Media for producing β-amylase | |
|---|---|
| | (w/v) |
| Corn steep liquor | 2% |
| Soluble starch | 4% |
| Calcium carbonate | 2% |

β-amylase activities in the obtained culture supernatants were measured in the above-described β-amylase measurement method. The results were shown in Table 2.

TABLE 2

| | Activity (u/ml) |
|---|---|
| DSM1316 | 4.0 |
| DSM1320 | 14.8 |
| DSM1667 | 4.0 |
| APC9451 | 5.7 |

2. Production and Purification of β-Amylase Derived from *Bacillus flexus* Apc9451

*Bacillus flexus* APC9451 was subjected to shaking culture at 30° C. for 3 days using a liquid medium having the compositions shown in Table 1. The obtained culture supernatant was concentrated 4 folds with a UF membrane (AIP-0013, manufactured by Asahi Kasei Corporation), and thereto was added ammonium sulfate to have a saturation concentration of 60%. The precipitated fraction was redissolved in a 20 mM acetic acid buffer solution (pH 5.5), and thereto was subsequently added ammonium sulfate to have a saturation concentration of 20%. The precipitate thus formed was removed by centrifugation and then passed through a HiPrep Butyl 16/10 FF column (GE Healthcare) equilibrated with a 20 mM acetic acid buffer solution (pH 5.5) containing ammonium sulfate having a saturation concentration of 20%, and the adsorbed β-amylase protein was eluted by an ammonium sulfate linear concentration gradient from 20% of a saturation concentration to 0% of a saturation concentration.

The collected β-amylase active fraction was concentrated with a UF membrane and then passed through a HiTrap CM FF column (manufactured by GE Healthcare Ltd.) equilibrated with a 20 mM acetic acid buffer solution (pH 5.5), and the adsorbed β-amylase protein was eluted by an NaCl linear concentration gradient from 0 M to 0.5 M.

Furthermore, the collected β-amylase active fraction was concentrated with a UF membrane, then passed through a HiLoad 16/60 Superdex 200 column (manufactured by GE Healthcare Ltd.) equilibrated with a 20 mM acetic acid buffer solution (pH 5.5) containing 0.15 M NaCl, and eluted with the same buffer solution. β-amylase active fractions were collected and then desalted and concentrated using an ultrafiltration membrane to obtain a purified enzyme sample. The obtained purified enzyme was subjected to examinations of the following various properties, and also subjected to an N-terminal amino acid sequence analysis and an internal peptide amino acid sequence analysis.

Figure 5:
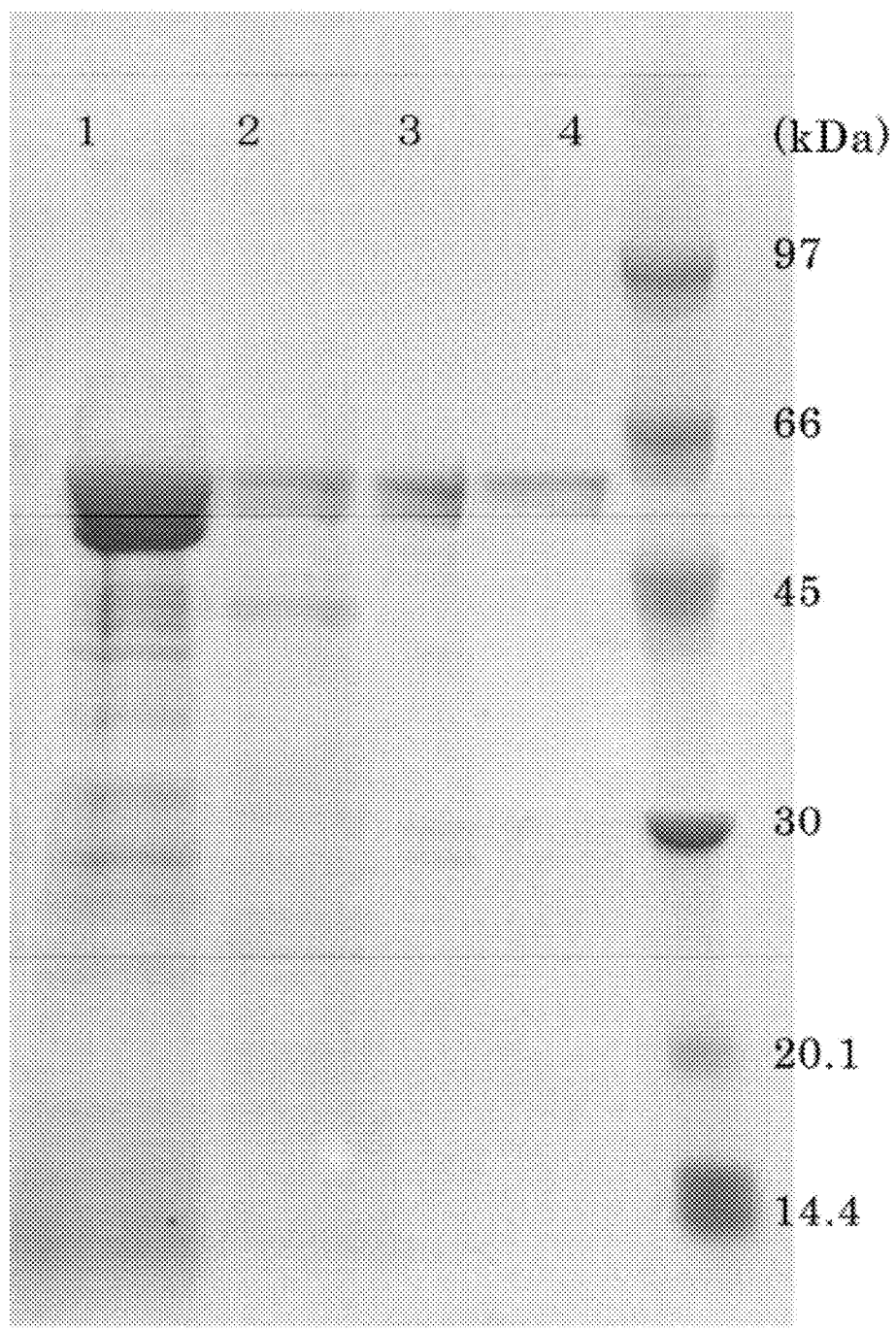
FIG. 5 is the result of SDS-PAGE for a purified β-amylase and a sample in the middle of purification. Lane 1: ammonium sulfate fraction, lane 2: HiPrepButyl 16/10 FF, lane 3: HiTrap CM FF, lane 4: HiLoad 16/60 Superdex200

Results of purification in respective stages were shown in Table 3. The specific activity in the final stage was 2270 times as compared to that of a crude enzyme. FIG. 5 shows results of SDS-PAGE (CBB staining) in a 10 to 20% gradient gel carried out on the respective steps of the purification process. The purified enzyme sample (lane 4) is found to be a single protein in SDS-PAGE.

TABLE 3

| | Total protein amount (mg) | Total activity (U) | Relative activity (u/mg) | Recovery rate (%) |
|---|---|---|---|---|
| Concentrated solution | 27200 | 18700 | 0.69 | 100 |
| Ammonium sulfate fraction | 2856 | 9054 | 3.17 | 48 |
| Butyl FF | 59.9 | 4120 | 68.8 | 22 |
| CM FF | 0.64 | 656 | 1031 | 4 |
| Superdex 200 | 0.084 | 132 | 1569 | 1 |

3. Various Properties of Heat Resistant β-Amylase (1) Optimum Reaction Temperature The purified enzyme was reacted at reaction temperatures of 25° C., 37° C., 50° C., 55° C., 60° C., 65° C. and 70° C. according to the above-described β-amylase activity measurement method. Activities were shown as relative activities assuming that a value at a temperature when the maximum activity is exhibited is 100%. The optimum reaction temperature was around at 55° C. (FIG. 1).

(2) Optimum Reaction pH

Figure 2:
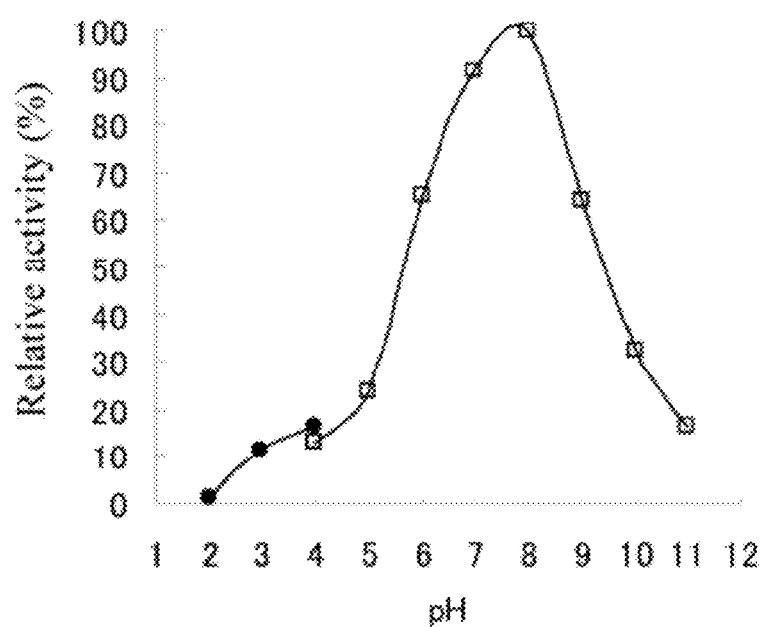
FIG. 2 is a graph showing an optimum pH of the β-amylase derived from *Bacillus flexus*. Black circles: citric acid buffer solution at pH 2, 3 and 4, white squares: Britton-Robinson buffer solution at pH 4, 5, 6, 7, 8, 9, 10 and 11

Activities were measured under the reaction conditions at 37° C. for 10 minutes in each buffer solution (citric acid buffer solution at pH 2, pH 3 and pH 4, and Britton-Robinson buffer solution at pH 4, pH 5, pH 6, pH 7, pH 8, pH 9, pH 10 and pH 11), using a 1% soluble starch as a substrate. Activities are shown as relative activities assuming that a pH value when the maximum activity is exhibited is 100%. The optimum reaction pH was around 8.0 (FIG. 2).

(3) Thermostability

Figure 3:
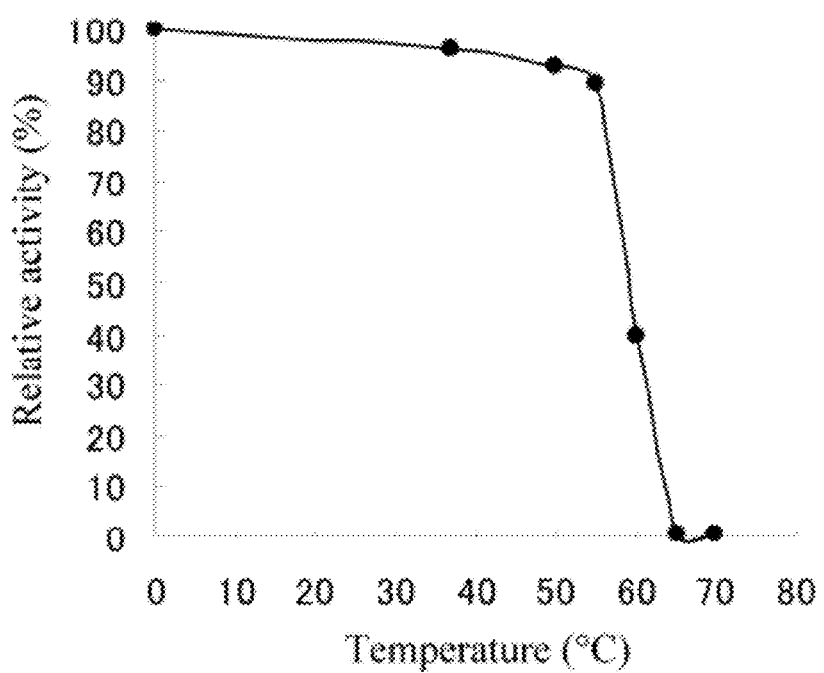
FIG. 3 is a graph showing thermostability of a β-amylase derived from *Bacillus flexus*.

A 20 U/ml enzyme solution was thermally treated for 10 minutes in a 0.1 M acetic acid-hydrochloric acid buffer solution (pH 5.0) which contains a 10 mM calcium acetate at respective temperatures of 37° C., 50° C., 55° C., 60° C., 65° C. and 70° C., and residual activities were then measured in the above-described β-amylase activity measurement method. The results were expressed as residual activity, assuming that the activity of the sample untreated with heat was 100%. After heat treatment at 55° C. for 10 minutes, the residual activity was 90% or more, and the activity was stable up to 55° C. (FIG. 3).

(4) pH Stability

Figure 4:
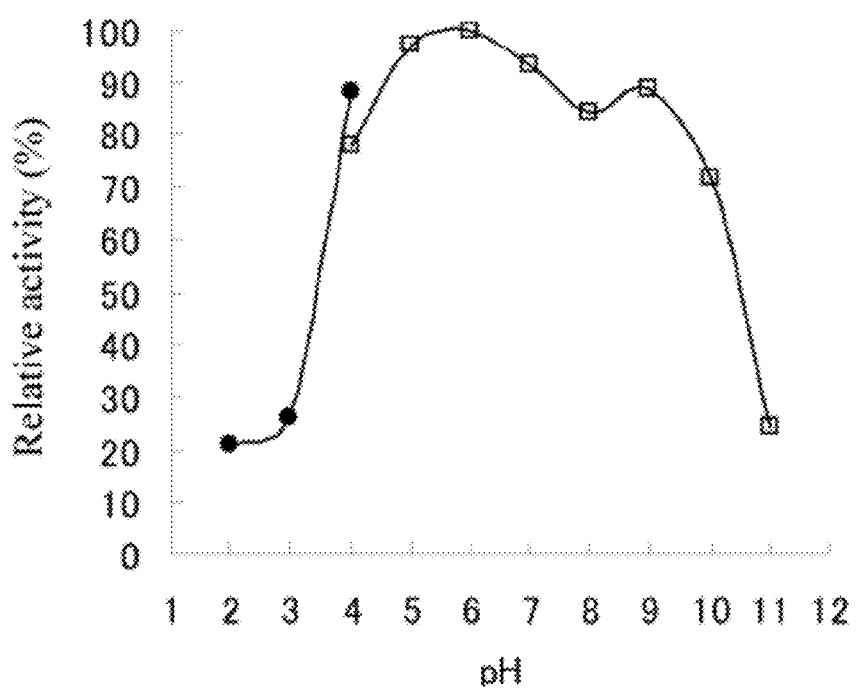
FIG. 4 is a graph showing pH stability of a β-amylase derived from *Bacillus flexus*. Black circles: citric acid buffer solution at pH 2, 3 and 4, white squares: Britton-Robinson buffer solution at pH 4, 5, 6, 7, 8, 9, 10 and 11

After treating at 30° C. for 3 hours in each buffer solution (citric acid buffer solution at pH 2, pH 3 and pH 4, and Britton-Robinson buffer solution at pH 4, pH 5, pH 6, pH 7, pH8, pH9, pH10 and pH11), activities were measured in the above-described β-amylase activity measurement method. The results were expressed as relative activity, assuming that the value at the pH at which the highest activity was exhibited was 100%. The optimum reaction pH was 4 to 9 (FIG. 4).

(5) Molecular Weight Measurement by SDS-PAGE

SDS-PAGE was carried out in accordance with the method of Laemmli, et al. A molecular weight marker used was a Low Molecular Weight Calibration Kit for Electrophoresis (GE Healthcare), and contained phosphorylase b (97,000 Da), albumin (66,000 Da), ovalbumin (45,000 Da), carbonic anhydrase (30,000 Da), trypsin inhibitor (20,100 Da) and α-lactalbumin (14,400 Da) as standard proteins. Electrophoresis was performed for about 80 minutes at 20 mA/gel using a gradient gel (Wako) having a gel concentration of 10 to 20%, and as a result of finding a molecular weight, the molecular weight was about 60 kDa (FIG. 5).

(6) Isoelectric Point

The isoelectric point of the present enzyme was about 9.7, as measured by isoelectric focusing (600V, 4° C., 48 hours) using Ampholine.

(7) Effects of Metallic Ion and Inhibitor 1 mM of various metallic ions and inhibitors were added respectively to a 0.1 M acetic acid-hydrochloric acid buffer solution (pH 5.0) containing a β-amylase and 10 mM calcium acetate and treated at 30° C. for 30 minutes, and activities were then measured in the above-described β-amylase activity measurement method. The results were shown in Table 4. The results were expressed as relative activity, assuming that the value in a case where the metallic ions and inhibitors were not added was 100%. The activities were shown as relative activities assuming that an activity in a case of no addition is 100%. The activities were inhibited by Cu ion, iode acetate, PCMB and SDS.

TABLE 4

|  | Relative activity (%) |
|---|---|
| $Na^+$ | 88 |
| $K^+$ | 96 |
| $Ca^{2+}$ | 130 |
| $Mn^{2+}$ | 222 |
| $Mg^{2+}$ | 103 |
| $Zn^{2+}$ | 96 |
| $Cu^{2+}$ | 46 |
| $Fe^{2+}$ | 105 |
| $Fe^{3+}$ | 113 |
| EDTA | 97 |
| N-ethylmaleimide | 93 |
| PCMB | 25 |
| Monoiodoacetic acid | 14 |
| SDS | 37 |
| No addition | 100 |

(8) Substrate Specificity

A β-amylase activity to each substrate was examined. The β-amylase activity was shown as a relative activity assuming that an activity to a soluble starch is 100%. A maltose generated amount was examined for oligosaccharides according to the maltose assay method shown below. 0.1 U/ml of an enzyme was reacted to 0.5% of each maltooligosaccharide at 37° C. for 30 minutes, and then a quantity of maltose was determined in HPLC (Aminex carbohydrate HPX-42A, BIO-RAD Co.). A relative activity to each maltooligosaccharide was determined from a maltose generated amount assuming that a maltose generated amount is 100% when a soluble starch was used as a substrate.

The results were shown in Table 5. The activities were shown as relative activities assuming that a maltose generated amount with respect to a soluble starch is 100%. Cyclodextrin, pullulan, and dextran were hardly digested. For oligosaccharides, the β-amylase was not acted on maltotriose and well acted on other oligosaccharides.

TABLE 5

| Substrates | Relative activity (%) |
|---|---|
| Maltotriose | 0 |
| Maltotetraose | 75 |
| Maltopentaose | 102 |
| Maltohexaose | 131 |
| Maltoheptaose | 111 |
| α-Cyclodextrin | 0 |
| β-Cyclodextrin | 1.4 |

TABLE 5-continued

| Substrates | Relative activity (%) |
|---|---|
| γ-Cyclodextrin | 0.6 |
| Amylose | 98 |
| Amylopectin | 83 |
| Pullulan | 3.4 |
| Dextran | 1.9 |
| Glycogen | 51 |
| Potato starch | 78 |
| Cornstarch | 85 |
| Waxy cornstarch | 106 |
| Soluble starch | 100 |

4. Acquisition of Gene Fragment Coding for β-Amylase Derived from *Bacillus flexus*

(a) Isolation of Chromosome DNA

Genomic DNA was prepared from a bacterial cell of *Bacillus flexus* obtained in 1 in the method of Saito and Miura (Biochim Biophys. Acta, 72, 619-629, 1963).

(b) Determination of Partial Amino Acid Sequence

A purified sample of the β-amylase obtained in (step) 1 was subjected to an amino acid sequence analysis to determine 10 residuals of an N-terminal amino acid sequence (SEQ ID NO: 1) and internal peptide amino acid sequences (SEQ ID NOS: 2, 3).

(c) Preparation of DNA Probe in PCR

Two types of mixed oligonucleotides were synthesized as PCR primers (SEQ ID NOS: 4, 5) based on the N-terminal amino acid sequence and internal amino acid sequence. Using these primers and chromosome DNA of *Bacillus flexus* as templates, a PCR reaction was carried out under the conditions shown below.

<PCR Reaction Solution>
10×PCR reaction buffer solution (TAKARA BIO INC.) 5.0 μl
dNTP mixed solution (each 2.5 mM, TAKARA BIO INC.) 4.0 μl
25 mM $MgCl_2$ 5 μl
100 μM sense primer 3.0 μl
100 μM antisense primer 3.0 μl
Distilled water 28.5 μl
Chromosome DNA solution (140 μg/ml) 1 μl
LA Taq DNA polymerase (TAKARA BIO INC.) 0.5 μl
<PCR Reaction Conditions>
Stage 1: denaturation (94° C., 5 min) 1 cycle
Stage 2: denaturation (94° C., 30 sec.) 30 cycles
Annealing (48° C., 30 sec.)
Extension (72° C., 1 mM)

About 0.86 kb of the obtained DNA fragment was cloned to pGEM-Teasy (Promega Co.) and then the base sequence was confirmed to find a base sequence coding for the partial amino acid sequence immediately after the sense primer and immediately before the antisense primer. The present DNA fragment was used as a DNA probe for cloning full-length gene.

(d) Preparation of Gene Library

As a result of a southern hybridization analysis of a chromosome DNA of *Bacillus flexus*, about 5.0 kb of a single band that is hybridized with a probe DNA was confirmed in the KpnI resolvent. In order to clone about 5.0 kb of the KpnI DNA fragment, a gene library was prepared as shown below. The chromosome DNA prepared in the above (a) was treated with KpnI. 28 μg of the genomic DNA of *Bacillus flexus*, 3 μl of a 10×L buffer solution, 26 μl of distilled water and 1 μl of KpnI were mixed to be treated at 37° C. for 15 hours. The digested product was ligated to a pUC19 (TAKARA BIO INC.) vector treated with KpnI to thus obtain a gene library.

(e) Screening of Gene Library 0.86 kb of the DNA fragment obtained in the above (c) was labeled using DIG-High Prime (Roche, Ltd.). Using the labeled DNA fragment as a DNA probe, the gene library obtained in (d) was screened by colony hybridization. A plasmid pUC19-BAF was obtained from the obtained positive colony.

(f) Determination of Base Sequence

The base sequence of the plasmid pUC19-BAF was determined according to an ordinary method. A base sequence (1638 bp) coding for the β-amylase is shown in SEQ ID NO: 6. An amino acid sequence (545 amino acids) coded by SEQ ID NO: 6 is shown in SEQ ID NO: 7. The N-terminal region amino acid sequence (SEQ ID NO: 1) and internal amino acid sequences (SEQ ID NOS: 2, 3), which were determined in (b), were found in the amino acid sequence.

5. Expression of β-Amylase Derived from *Bacillus flexus* in *E. coli*

(a) Construction of Expression Plasmid of β-Amylase in *E. coli*

Based on DNA sequences coding for an N-terminal region amino acid sequence and a C-terminal region amino acid sequence, 2 types of oligonucleotides (SEQ ID NOS: 8, 9) were synthesized as PCR primers. A NdeI restriction enzyme recognition site was added to a sense primer and a XhoI restriction enzyme recognition site was added to an antisense primer. Using these primers and plasmid pUC19-BAF having β-amylase gene as templates, a PCR reaction was carried out under the conditions shown below.

<PCR Reaction Solution>
10×PCR reaction buffer solution (TOYOBO CO., LTD.) 5.0 μl
dNTP mixed solution (each 2.5 mM, TOYOBO CO., LTD.) 5.0 μl
10 μM sense primer 1.5 μl
10 μM antisense primer 1.5 μl
25 mM MgSO₄ 2 μl
Distilled water 33 μl
Plasmid pUC19-BAF solution (83 μg/ml) 1.0 μl
KOD-Plus-DNA polymerase (TOYOBO CO., LTD.) 1.0 μl
<PCR Reaction Conditions>
Stage 1: denaturation (94° C., 2 min) 1 cycle
Stage 2: denaturation (94° C., 15 sec.) 30 cycles
Annealing (60° C., 30 sec.)
Extension (68° C., 2 mM)

Figure 6:
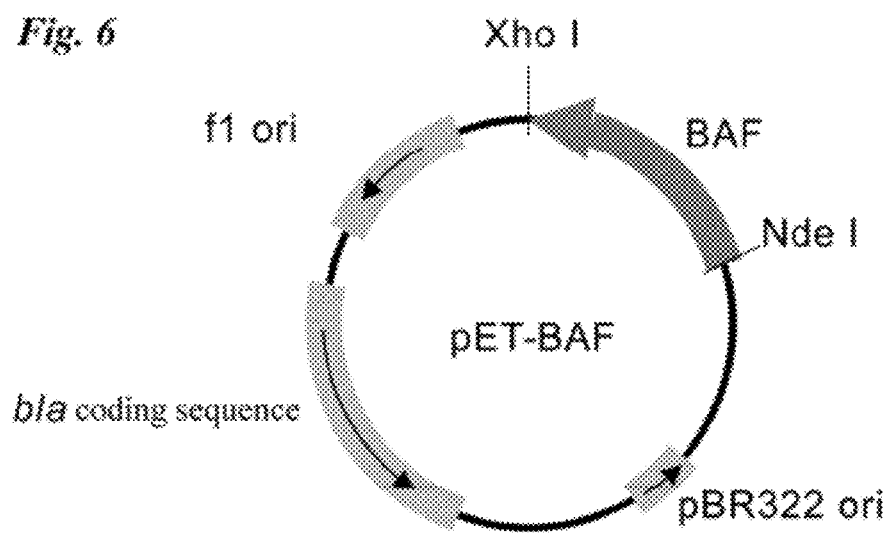
FIG. 6 shows a structure of expression plasmid pET-BAF.

The obtained PCR product was confirmed in electrophoresis, then purified with GENE CLEANE III (34 μl), thereto were added 4 μl of a 10×H buffer solution, 1 μl of NdeI and 1 μl of XhoI, and the reaction mixture was treated with an enzyme at 37° C. for 15 hours. A restriction enzyme treated solution was confirmed in electrophoresis, purified and then ligated to a vector pET20 (b) (TAKARA BIO INC.) that had been previously treated with NdeI and XhoI to thus obtain an expression plasmid pET-BAF (FIG. 6). It was also confirmed that a base sequence coding for the β-amylase in pET-BAF was correct.

(b) Expression of β-Amylase in *E. coli*

Expression plasmid pET-BAF was introduced into *E. coli* BL21 (DE3) (Novagen). A strain having pET-BAF into which a β-amylase gene of interest is inserted was selected from a transformant obtained as an ampicillin resistant strain in colony PCR. A transformant of *E. coli* BL21 (DE3) having an expression vector pET20 (b) was also obtained as a control. These transformants were cultured in 4 ml of an LB medium containing 50 μg/ml of ampicillin at 18° C., 160 rpm for 47 hours to collect bacteria. The bacterial cells were suspended in 0.5 ml of a 20 mM acetic acid buffer solution (pH 5.5) and 0.25 g of glass beads with 0.1 mmφ were added thereto to crush the bacterial cells by a multi-beads shocker (manufactured by Yasui Kikai Corporation). For the crushing condition, 3.5 cycles of ON for 30 seconds and OFF for 30 seconds were repeated. The obtained cell free-extract was subjected to centrifugation to thus obtain a soluble component.

Results of performing an activity measurement on the obtained sample according to the β-amylase activity measurement method were shown in Table 6 below.

TABLE 6

|  | Activity (U/ml) | Protein (mg/ml) | Relative activity (U/mg) |
|---|---|---|---|
| pET-BAF | 43.5 | 7.9 | 5.5 |
| pET20(b) | 0.4 | 8.0 | 0.05 |

<β-amylase activity measurement method (2)>

A β-amylase activity was measured also in the following method. That is, 1 ml of an enzyme solution was added to 10 ml of a 0.05 M acetic acid-sodium acetate buffer solution (pH 5.0) containing 0.5% soluble starch, and the mixture was incubated at 40° C. for 30 minutes, thereafter adding 4 ml of a Fehling's reagent (1.25 M NaOH, 0.62 M potassium sodium tartrate tetrahydrate, 0.14 M copper sulfate (II) pentahydrate) to terminate the reaction. After termination of the reaction, the reaction solution was boiled for 2 minutes and thereto were added 2 ml of a 2.26 M potassium iodide reagent and 2 ml of a 0.25% sulfuric acid reagent to perform titration with a 0.005 mol/L sodium thiosulfate solution. An enzyme amount that enhances reducing ability corresponding to 10 mg of glucose in 30 minutes of a reaction time is assumed to be 1 unit (U). Activity values measured in this method are used in examples below.

6. Production of Maltose Syrup Using β-Amylase Derived from *Bacillus flexus*

6-1. Effects of Substrate Concentration

A dextrin solution (manufactured by Nissi Co., Ltd., NSD100) was adjusted from 20% to 35%, 0.6 U/g-DS of a β-amylase derived from *Bacillus flexus* was added to the solution and them react at pH 5.8, 62° C. for 42 hours. The sugar composition after the reaction was analyzed in a high performance liquid chromatography column MCI GEL CK04S (manufactured by Mitsubishi Chemical Corporation), and the results were shown in Table 7. Accordingly, a high maltose production ability was shown also in high concentration dextrin.

TABLE 7

| Substrate concentration | G1 | G2 | G3 | G4 | G5≤ |
|---|---|---|---|---|---|
| 20% | 0.00% | 56.38% | 7.37% | 1.57% | 34.68% |
| 25% | 0.00% | 57.48% | 7.29% | 1.11% | 34.12% |
| 30% | 0.00% | 57.85% | 7.28% | 0.98% | 33.89% |
| 35% | 0.00% | 57.42% | 7.29% | 1.02% | 34.27% |

6-2. Effects of Reaction Temperature

4 U/g-DS of a β-amylase derived from *Bacillus flexus* was added to a 30% dextrin solution (manufactured by Nissi Co., Ltd., NSD100) (pH 5.8), and them react at 56° C. and 65° C. for 42 hours. The sugar composition after the reaction was analyzed in a high performance liquid chromatography column MCI GEL CK04S (manufactured by Mitsubishi Chemical Corporation), and the results were shown in Table 8. Accordingly, a high maltose production ability was shown also at a high temperature.

TABLE 8

| Temperature | G1 | G2 | G3 | G4 | G5≤ |
|---|---|---|---|---|---|
| 56° C. | 0.20% | 59.81% | 7.60% | 0.78% | 31.61% |
| 65° C. | 0.17% | 59.50% | 7.33% | 0.75% | 32.25% |

6-3. Effects of Reaction pH and Combination with Debranching Enzyme

A β-amylase and a debranching enzyme were combined at various pH and a maltose syrup was produced from dextrin. A 30% dextrin solution (manufactured by Nissi Co., Ltd., NSD100) was adjusted from pH 5.8 to 7.0 and added with 1 U/g-DS of a β-amylase and 3.3 μl/g-DS of Kleistase PLF (manufactured by Daiwa Fine Chemicals Co., Ltd.) as a debranching enzyme were added to the solution and them react at 62° C. for 42 hours. The sugar composition after the reaction was analyzed in a high performance liquid chromatography column MCI GEL CK04S (manufactured by Mitsubishi Chemical Corporation), and the results were shown in Table 9.

TABLE 9

| pH | G1 | G2 | G3 | G4 | G5≤ |
|---|---|---|---|---|---|
| pH 5.8 | 0.16% | 80.48% | 12.72% | 2.64% | 4.00% |
| pH 6.0 | 0.17% | 78.08% | 12.46% | 2.92% | 6.37% |
| pH 6.5 | 0.18% | 76.76% | 12.34% | 2.72% | 8.00% |
| pH 7.0 | 0.22% | 69.57% | 11.22% | 2.92% | 16.07% |

Accordingly, combination of a debranching enzyme made it possible to produce 80% or more of maltose. Furthermore, a sufficient production ability was shown also in a neutral zone.

Figure 7:
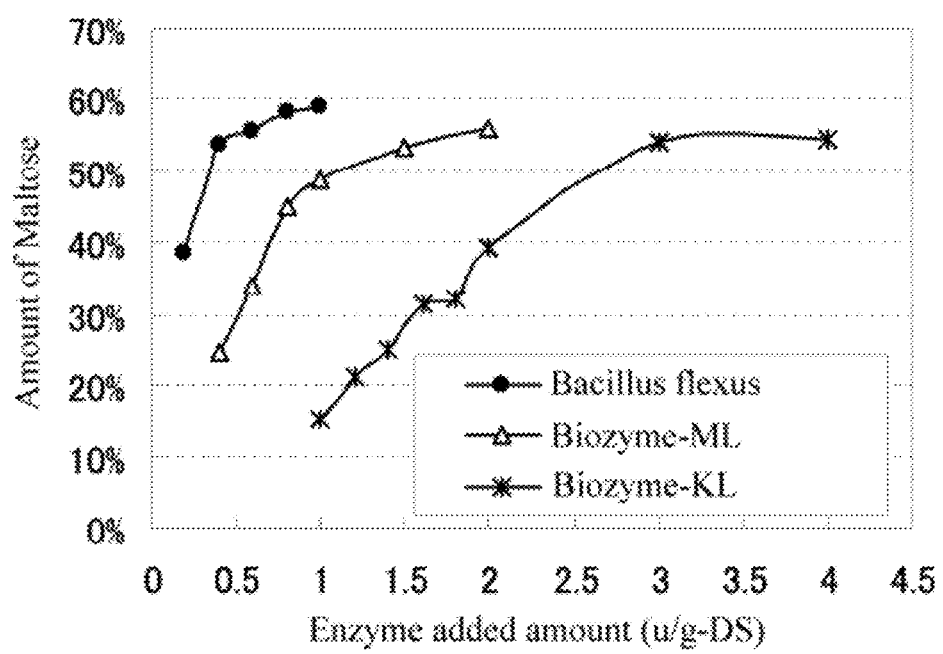
FIG. 7 is a graph showing comparison of the amounts of maltose generated. The amount of maltose was compared between three β-amylases (derived from *Bacillus flexus*, derived from soybean, and derived from wheat).

6-4. Effects of Enzyme Adding Amount and Comparison to β-Amylases Derived from Barley and Derived from Wheat A β-amylase derived from Bacillus flexus, Biozyme ML (barley β-amylase, manufactured by Amano Enzyme Inc.), and Biozyme KL (wheat β-amylase, manufactured by Amano Enzyme Inc.) were added to a 30% dextrin solution (NSD100, manufactured by manufactured by Nissi Co., Ltd.), and reactions were carried out at pH 5.8, 62° C. for 42 hours in the case of the β-amylase derived from Bacillus flexus, and at pH 5.5, 58° C. for 42 hours in the other cases. The sugar compositions after the reactions were analyzed in a high performance liquid chromatography column MCI GEL CK04S (manufactured by Mitsubishi Chemical Corporation), and the results were shown in FIG. 7 and Table 10.

TABLE 10

| Enzymes | Amounts (U/g-DS) | G1 | G2 | G3 | G4 | G5≤ |
|---|---|---|---|---|---|---|
| β-amylase derived from Bacillus flexus | 0.2 | 0.12% | 38.68% | 6.59% | 4.94% | 49.67% |
| | 0.4 | 0.16% | 53.70% | 7.08% | 2.46% | 36.60% |
| | 0.6 | 0.13% | 55.60% | 6.99% | 1.12% | 36.16% |
| | 0.8 | 0.15% | 58.38% | 7.20% | 0.83% | 33.44% |
| | 1.0 | 0.15% | 59.14% | 7.16% | 0.74% | 32.81% |
| Biozyme-ML | 0.4 | 0.12% | 24.44% | 4.09% | 4.71% | 66.64% |
| | 0.6 | 0.13% | 33.96% | 5.26% | 5.10% | 55.55% |
| | 0.8 | 0.14% | 45.09% | 6.83% | 4.56% | 43.38% |
| | 1.0 | 0.00% | 48.77% | 7.04% | 3.44% | 40.75% |
| | 1.5 | 0.13% | 53.27% | 6.99% | 1.24% | 38.37% |
| | 2.0 | 0.15% | 56.05% | 7.15% | 0.78% | 35.87% |
| Biozyme-KL | 1.0 | 0.00% | 15.12% | 3.32% | 3.80% | 77.76% |
| | 1.2 | 0.11% | 21.16% | 3.94% | 4.42% | 70.37% |
| | 1.4 | 0.11% | 25.14% | 4.42% | 4.69% | 65.64% |
| | 1.6 | 0.14% | 31.49% | 5.31% | 5.11% | 57.59% |
| | 1.8 | 0.12% | 32.25% | 5.47% | 4.76% | 57.40% |
| | 2.0 | 0.14% | 39.47% | 6.42% | 4.80% | 49.17% |
| | 3.0 | 0.00% | 54.15% | 7.16% | 1.09% | 37.60% |
| | 4.0 | 0.00% | 54.30% | 6.69% | 0.76% | 37.98% |

Accordingly, the β-amylase derived from Bacillus flexus generated 59.14% of maltose with an adding amount of 1.0 U/g-DS, which was apparently excellent as compared to a maltose generated amount of 56.06% in the case of an adding amount of 2.0 U/g-DS of the barley enzyme and a maltose generated amount of 54.30% in the case of an adding amount of 4.0 U/g-DS of the wheat enzyme.

Figure 8:
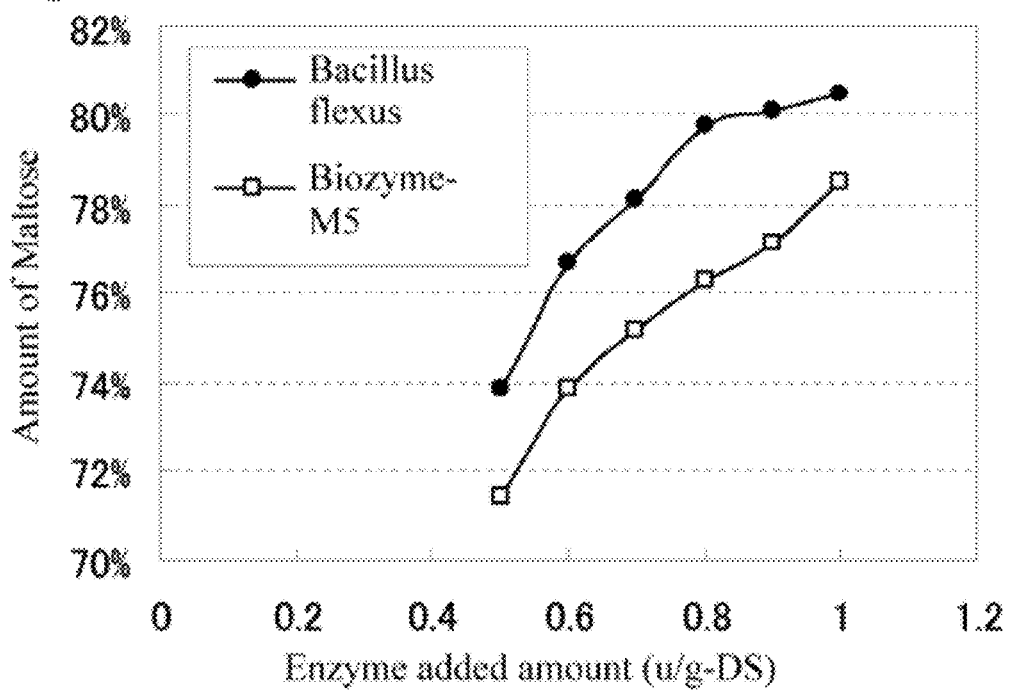
FIG. 8 is a graph showing comparison of the amount of maltose generated. The amount of maltose was compared between two β-amylases (derived from *Bacillus flexus* and derived from soybean).

6-5. Effects of Enzyme Adding Amount and Comparison to β-Amylase Derived from Soybean A β-amylase derived from Bacillus flexus or Biozyme M5 (soybean β-amylase, manufactured by Amano Enzyme Inc.), and 3.3 μl/g-DS of Kleistase PLF (manufactured by Daiwa Fine Chemicals Co., Ltd.) as a debranching enzyme were added to a 30% dextrin solution (NSD100, manufactured by Nissi Co., Ltd.), and reactions were carried out at 62° C., pH 5.8 for 42 hours in the case of the β-amylase derived from Bacillus flexus, and at 62° C., pH 5.5 for 42 hours in the case of the soybean enzyme. The sugar compositions after the reactions were analyzed in a high performance liquid chromatography column MCI GEL CK04S (manufactured by Mitsubishi Chemical Corporation), and the results were shown in FIG. 8 and Table 11.

TABLE 11

| Enzymes | Amounts (U/g-DS) | G1 | G2 | G3 | G4 | G5≤ |
|---|---|---|---|---|---|---|
| β-amylase derived from Bacillus flexus | 0.5 | 0.16% | 73.88% | 12.27% | 4.64% | 9.05% |
| | 0.6 | 0.15% | 76.67% | 12.49% | 3.81% | 6.88% |
| | 0.7 | 0.16% | 78.14% | 12.56% | 3.31% | 5.83% |
| | 0.8 | 0.12% | 79.75% | 12.88% | 3.21% | 4.04% |
| | 0.9 | 0.17% | 80.10% | 12.74% | 2.79% | 4.20% |
| | 1.0 | 0.16% | 80.48% | 12.72% | 2.64% | 4.00% |
| Biozyme-M5 | 0.5 | 0.15% | 71.46% | 11.69% | 2.82% | 13.88% |
| | 0.6 | 0.15% | 73.90% | 11.95% | 2.58% | 11.42% |
| | 0.7 | 0.14% | 75.15% | 12.06% | 2.43% | 10.22% |
| | 0.8 | 0.15% | 76.32% | 12.14% | 2.36% | 9.03% |
| | 0.9 | 0.15% | 77.18% | 12.23% | 2.34% | 8.10% |
| | 1.0 | 0.15% | 78.51% | 12.40% | 1.38% | 7.56% |

Accordingly, the β-amylase derived from Bacillus flexus generated 80.48% of maltose with an adding amount of 1.0 U/g-DS, which was apparently excellent as compared to a maltose generated amount of 78.51% in the case of an adding amount of 1.0 U/g-DS of the soybean enzyme.

6-6. Combination with α-Amylase (1)

A 30% dextrin solution (NSD100, manufactured by Nissi Co., Ltd.) (pH 5.8) was prepared, 0.5 U/g-DS of a β-amylase derived from Bacillus flexus, and 3.3 μl/g-DS of Kleistase PLF (manufactured by Daiwa Fine Chemicals Co., Ltd.) as a debranching enzyme were added to the solution and them react at 62° C. for 42 hours. An α-amylase agent Kleistase L1 (derived from bacteria, manufactured by Daiwa Fine Chemicals Co., Ltd.) was added to the reaction solution in amounts of 0.198, 0.264, and 0.330 μl/g-DS to react for further 6 and 24 hours. The sugar compositions after the reaction were analyzed in a high performance liquid chromatography column MCI GEL CK04S (manufactured by Mitsubishi Chemical Corporation), and the results were shown in Table 12.

TABLE 12

| Amount of Kleistase L1 (µl/g-DS) | Reaction time (h) | G1 | G2 | G3 | G4 | G5≤ |
|---|---|---|---|---|---|---|
| Before addition | 0 | 0.18% | 73.00% | 12.37% | 5.27% | 9.18% |
| 0.198 | 6 | 0.19% | 74.51% | 13.04% | 5.58% | 6.68% |
|  | 24 | 0.21% | 75.56% | 13.84% | 6.31% | 4.08% |
| 0.264 | 6 | 0.19% | 74.12% | 13.10% | 5.64% | 6.95% |
|  | 24 | 0.22% | 75.51% | 13.92% | 6.37% | 3.98% |
| 0.330 | 6 | 0.19% | 74.87% | 13.35% | 5.78% | 5.81% |
|  | 24 | 0.26% | 75.41% | 13.97% | 6.42% | 3.94% |

Accordingly, addition of an α-amylase made it possible to improve a maltose yield and also reduce G5 or more high molecular oligosaccharides. Thus, improvement in a filtration property after the reaction can be expected.

6-7. Combination with α-Amylase (2)

A 30% dextrin solution (NSD100, manufactured by Nissi Co., Ltd.) (pH 5.8) was prepared, 0.6 U/g-DS of a β-amylase derived from *Bacillus flexus*, 3.3 µl/g-DS of Kleistase PLF (manufactured by Daiwa Fine Chemicals Co., Ltd.) as a debranching enzyme, and 0.02 µl/g-DS of Kleistase L1 (derived from bacteria, manufactured by Daiwa Fine Chemicals Co., Ltd.) as an α-amylase agent were added to the solution and then react at 62° C. for 42 hours. The sugar composition after the reaction was analyzed in a high performance liquid chromatography column MCI GEL CK04S (manufactured by Mitsubishi Chemical Corporation), and the results were shown in Table 13.

TABLE 13

| α-amylase | G1 | G2 | G3 | G4 | G5≤ |
|---|---|---|---|---|---|
| No addition | 0.16% | 62.52% | 11.48% | 6.62% | 19.22% |
| Kleistase L1 | 0.25% | 65.96% | 16.00% | 9.06% | 8.73% |

Accordingly, addition of an α-amylase made it possible to improve a maltose yield and also reduce G5 or more high molecular oligosaccharides. Thus, improvement in a filtration property after the reaction can be expected.

6-8. Combination with α-Amylase (3)

A 30% dextrin solution (NSD100, manufactured by Nissi Co., Ltd.) (pH 5.8) was prepared, 0.6 U/g-DS of a β-amylase derived from *Bacillus flexus* and 0.10 µl/g-DS of Biozyme L (derived from *Aspergillus oryzae*, manufactured by Amano Enzyme Inc.) as an α-amylase agent were added to the solution and then react at 62° C. for 42 hours. The sugar composition after the reaction was analyzed in a high performance liquid chromatography column MCI GEL CK04S (manufactured by Mitsubishi Chemical Corporation), and the results were shown in Table 14.

TABLE 14

| α-amylase | G1 | G2 | G3 | G4 | G5≤ |
|---|---|---|---|---|---|
| No addition | 0.17% | 27.34% | 5.83% | 5.49% | 61.17% |
| Kleistase L1 | 0.21% | 33.09% | 14.95% | 11.72% | 40.03% |

Accordingly, addition of an α-amylase made it possible to improve a maltose yield and also reduce G5 or more high molecular oligosaccharides. Thus, improvement in a filtration property after the reaction can be expected.

7. Effects of β-Amylase on Bread Making

A β-amylase was added to dough when making bread. Basic ingredients for angular bread (hard flour 260 g; sugar 13 g; salt 5.2 g; shortening 10.4 g; L-ascorbic acid 0.013 g; cold water 192 g; dry yeast 3.1 g), or these ingredients with 80 U of a β-amylase were supplied to an automatic bread bakery SD-BT50 (manufactured by Panasonic Corporation).

After firing, bread was stood to cool at 26° C. for 1 hour, then put in a plastic bag in order to avoid water evaporation, and preserved at 26° C. After preservation for 1 or 5 days, the bread was sliced to a thickness of 2 cm, and the center of the bread was cut into a cylinder having a diameter of 47 mm. The bread hardness was measured using a FUDOH rheometer NRM-2002J (manufactured by RHEOTECH Co., Ltd.) as a maximum load in the case of 1.5 cm compression at a compression speed of 2 mm/min. The results were shown in Table 15.

TABLE 15

|  | Softness | |
|---|---|---|
|  | 1 day after | 5 days after |
| Enzyme-containing samples | 100% | 151% |
| Enzyme-free samples | 100% | 207% |

In an enzyme-free samples and an enzyme-containing samples, bread hardnesses after preservation for 5 days were compared, assuming that each bread hardness after preservation for 1 day was 100%. As a result, the hardness was increased to 151% in enzyme-containing samples %, and as compared to those in the enzyme-free samples (207%), hardening of the bread was suppressed and softness was maintained.

8. Effects of β-Amylase on Retrogradation of Rice Cake 165 g of water was added to 200 g of rice flour and then supplied to a KitchenAid mixer KSM5 (manufactured by KitchenAid) to uniform the ingredients with a flat beater, thereafter steaming over high heat for 15 minutes to obtain rice cake dough. The obtained rice cake dough was again supplied to the KitchenAid mixer and kneaded with a dough hook. After the dough temperature was cooled to 55° C., 120 U of a β-amylase was added to the dough and the dough was kneaded for 3 minutes so as to be uniformly dispersed and rice cakes were thus obtained. The obtained rice cakes were filled in petri dishes so as not to contain air, and allowed to stand respectively at 4° C., 15° C., and 25° C. for 3 days. On each day, each rice cake was hollowed out into a cylinder having a diameter of 28 mm, and a stress was measured in the case of 5 mm compression at a compression speed of 2 mm/min with a plunger having a diameter of 15 mm, using a FUDOH rheometer NRM-2002J (manufactured by RHEOTECH Co., Ltd.). The results were shown in FIG. 9. The enzyme-containing samples had no change in the stresses as compared to the enzyme-free samples, that is, it was revealed that the hardness of the rice cake was inhibited. The effect on hardening inhibition was observed even in low temperature preservation.

9. Effects of β-Amylase on Steamed Rice 75 g of rice that was washed. After addition of 150 mL of water or 150 mL of water plus 30 U of a β-amylase, they were allowed to stand at room temperature for 2 hours, thereafter cooking in an ordinary method to obtain steamed rice. The obtained steamed rice were preserved at 4° C. for 7 days. The degrees of gelatinization before and after preservation were measured in the BAP method. The results were shown in Table 16.

TABLE 16

|  | Degree of gelatinization | |
| --- | --- | --- |
|  | 1 day after | 7 days after |
| Enzyme-containing samples | 96.2% | 62.9% |
| Enzyme-free samples | 95.3% | 59.7% |

The degrees of gelatinization in the BAP methods in the enzyme-containing samples were 96.2% immediately after steaming rice and 62.9% after 7 days. On the other hand, the degrees of gelatinization in the enzyme-free samples were 95.3% immediately after steaming rice and 59.7% after 7 days. Decrease in a degree of gelatinization was suppressed in the enzyme-containing samples, that is, retrogradation process of starch was suppressed.

INDUSTRIAL APPLICABILITY

The β-amylase of the present invention shows heat resistance which is comparable with a β-amylase derived from soybean, and is suitable in applications which require a reaction under a high temperature. Use of the β-amylase of the present invention makes it possible to perform an enzyme reaction at a high temperature where a possibility of contamination is small. Therefore, the β-amylase of the present invention is particularly useful in applications such as saccharification of starch including production of a maltose syrup, or food processing such as improvement of bread or dough, prevention of retrogradation of rice cakes or rice cake sweets, and prevention of retrogradation of steamed rice.

The invention is not limited by description of the embodiments and examples of the invention described above at all. Various modified embodiments are also included in the invention within the range that a person skilled in the art can easily conceived of, without departing from the description of the scope of patent claims.

Contents of treatises, unexamined patent publications, and examined patent publications specified in this specification are all incorporated herewith by their references.

[Sequence Listing Free Text]

SEQ ID NOS: 4, 5, 8, 9: explanation of artificial sequences: primer

The invention claimed is:

1. A method of processing a food, comprising: contacting a food comprising a polysaccharide or an oligosaccharide having an α-1,4 bond of glucose as the main chain with a β-amylase obtained from *Bacillus flexus*, wherein the β-amylase comprises an amino acid sequence at least 95% identical to the sequence set forth in SEQ ID NO: 7, and has the following enzymological properties:
   (1) action: having hydrolytic activity on polysaccharides and oligosaccharides to release maltose, whereas glucose is hardly released;
   (2) substrate specificity: having hydrolytic activity on starch, amylose, amylopectin, glycogen, maltotetraose, maltopentaose, maltohexaose, maltoheptaose, but having no substantial hydrolytic activity on pullulan, dextran, cyclodextrin, maltotriose;
   (3) thermostability: stable at 55° C. or lower (pH 5.0, for 10 minutes); and
   (4) molecular weight: about 60,000 (SDS-PAGE).

2. The method of processing a food according to claim 1, wherein the food is any one selected from the group consisting of bread or dough, rice cakes or rice cake sweets, and steamed rice or steamed rice processed products.

3. The method of processing a food according to claim 1, wherein the β-amylase has the following enzymological properties:
   (1) optimum temperature: about 55° C.,
   (2) optimum pH: about 8.0, and
   (3) pH stability: stable at pH 4 to 9 (30° C., for 3 hours).

4. The method of processing a food according to claim 1, wherein the β-amylase comprises the amino acid sequence set forth in SEQ ID NO: 7.

5. The method of processing a food according to claim 1, wherein other enzymes are acted in addition to the β-amylase.

6. The method of processing a food according to claim 5, wherein the other enzymes are one or more enzymes selected from the group consisting of lipase, phospholipase, glucose oxidase, xylanase, protease, transglutaminase, protein glutaminase, a debranching enzyme, pullulanase, isoamylase, α-amylase, glucoamylase and maltogenic α-amylase.

7. A method of processing a food, comprising: contacting a food comprising a polysaccharide or an oligosaccharide having an α-1,4 bond of glucose as the main chain with a β-amylase obtained from *Bacillus flexus*, wherein the β-amylase comprises an amino acid sequence at least 95% identical to the sequence set forth in SEQ ID NO:7.

8. The method of processing a food according to claim 1 or claim 7, wherein the β-amylase consists of SEQ ID NO:7.

* * * * *